(12) United States Patent
Kovatchev et al.

(10) Patent No.: US 7,815,569 B2
(45) Date of Patent: Oct. 19, 2010

(54) METHOD, SYSTEM AND COMPUTER PROGRAM PRODUCT FOR EVALUATING THE ACCURACY OF BLOOD GLUCOSE MONITORING SENSORS/DEVICES

(75) Inventors: Boris P. Kovatchev, Charlottesville, VA (US); Linda Gonder-Frederick, Charlottesville, VA (US); Daniel J. Cox, Charlottesville, VA (US); William L. Clarke, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 869 days.

(21) Appl. No.: 11/578,831

(22) PCT Filed: Apr. 21, 2005

(86) PCT No.: PCT/US2005/013792

§ 371 (c)(1),
(2), (4) Date: Oct. 18, 2006

(87) PCT Pub. No.: WO2005/106017

PCT Pub. Date: Nov. 10, 2005

(65) Prior Publication Data

US 2007/0232878 A1    Oct. 4, 2007

Related U.S. Application Data

(60) Provisional application No. 60/564,195, filed on Apr. 21, 2004.

(51) Int. Cl.
*A61B 5/00* (2006.01)
(52) U.S. Cl. .................. 600/365; 600/316; 600/319
(58) Field of Classification Search ................. 600/319, 600/365, 310, 316
See application file for complete search history.

(56) References Cited

U.S. PATENT DOCUMENTS 5,077,476 A    12/1991    Rosenthal
6,097,975 A    8/2000    Petrovsky (Continued)

FOREIGN PATENT DOCUMENTS

WO    WO 01/72208    10/2001

(Continued)

OTHER PUBLICATIONS

Chen, E. T., "Performance Evaluation of Blood Glucose Monitoring Devices", Diabetes Technology & Therapeutics, 2003, p. 749-768, vol. 5, No. 5.

(Continued)

*Primary Examiner*—Robert L Nasser
*Assistant Examiner*—Michael D'Angelo
(74) *Attorney, Agent, or Firm*—Novak Druce DeLuca + Quigg LLP; Robert J. Decker

(57) ABSTRACT

Continuous Glucose Error-Grid Analysis (CG-EGA) method, system or computer program product designed for evaluation of continuous glucose sensors providing frequent BG readings. The CG-EGA estimates the precision of such sensors/devices in terms of both BG values and temporal characteristics of BG fluctuation. The CG-EPA may account for, among other things, specifics of process characterization (location, speed and direction), and for biological limitations of the observed processes (time lags associated with interstitial sensors).

100 Claims, 12 Drawing Sheets

U.S. PATENT DOCUMENTS

| | | | |
|---|---|---|---|
| 6,181,957 B1 | 1/2001 | Lambert | |
| 6,424,850 B1 | 7/2002 | Lambert | |
| 6,477,393 B1 | 11/2002 | Chou | |
| 6,526,298 B1* | 2/2003 | Khalil et al. | 600/310 |
| 6,574,490 B2 | 6/2003 | Abbink | |
| 6,574,501 B2 | 6/2003 | Lambert | |
| 6,633,722 B1 | 10/2003 | Kohara et al. | |
| 6,654,620 B2 | 11/2003 | Wu | |
| 6,675,030 B2 | 1/2004 | Ciurczak | |
| 6,682,933 B2 | 1/2004 | Patel | |
| 6,813,519 B2 | 11/2004 | Lebel | |
| 6,853,854 B1 | 2/2005 | Proniewicz | |
| 6,865,408 B1 | 3/2005 | Abbink | |
| 7,025,425 B2 | 4/2006 | Kovatchev | |
| 2005/0214892 A1 | 9/2005 | Kovatchev | |
| 2008/0287766 A1* | 11/2008 | Rasdal et al. | 600/365 |

FOREIGN PATENT DOCUMENTS

| | | |
|---|---|---|
| WO | WO 2004/015539 | 2/2004 |

OTHER PUBLICATIONS

Clarke, W. L., "Evaluating Clinical Accuracy of Systems for Self-Monitoring of Blood Glucose", Diabetes Care, 1987, p. 622-628, vol. 10, No. 5.

Cox, D. J., "Accuracy of Perceiving Blood Glucose in IDDM", Diabetes Care, 1985, p. 529-536, vol. 8, No. 6.

Cox, D. J., "The Effects of Glucose Fluctuation on Cognitive Function and QOL: The Functional Costs of Hypoglycemia and Hyperglycemia Among Adults With Type 1 or Type 2 Diabetes", International Journal of Clinical Practice Supplement 129, 2002, p. 20-26.

Cox, D. J., "Understanding Error Grid Analysis", Diabetes Care, 1997, p. 911-912, vol. 20, No. 6.

Derr, R., "Is HbA1c Affected by Glycemic Instability?", Diabetes Care, 2003, p. 2728-2733, vol. 26, No. 10.

Djakoure-Platonoff, C., "Accuracy of the Continuous Glucose Monitoring System in Inpatient and Outpatient Conditions", Diabetes & Metabolism, 2003, p. 159-162, vol. 29, Issue 2.

Feldman, B., "A Continuous Glucose Sensor Based on Wired Enzyme Technology-Results From a 3-Day Trial in Patients With Type 1 Diabetes", Diabetes Technology & Therapeutics, 2003, p. 769-779, vol. 5, No. 5.

Gavin, J. R., "The Importance of Postprandial Hyperglycaemia", International Journal of Clinical Practice Supplement 107, 1999, p. 14-17.

Gross, T. M., "Performance Evaluation of the MiniMed® Continuous Glucose Monitoring System During Patient Home Use", Diabetes Technology & Therapeutics, 2000, p. 49-56, vol. 2, No. 1.

Haffner, S., "The Importance of Postprandial Hyperglycaemia in Development of Cardiovascular Disease in People With Diabetes: Point", International Journal of Clinical Practice Supplement 123, 2001, p. 24-26.

Hanefeld, M., "Postprandial Hyperglycaemia: Noxious Effects on the Vessel Wall", International Journal of Clinical Practice Supplement 129, 2002, p. 45-50.

Hanefeld, "Post-Prandial Hyperglycaemia and Vascular Disease", International Journal of Clinical Practice Supplement 112, 2000, p. 13-18.

Hanefeld, M., "Risk Factors for Myocardial Infarction and Death in Newly Detected NIDDM: The Diabetes Intervention Study, 11 Year-Follow-Up", Diabetologia, 1996, p. 1577-1583, vol. 39, No. 12.

Hanefeld, M., "The Postprandial State and the Risk of Atherosclerosis", Diabetic Medicine, 1997, p. S6-S11, vol. 14, Issue S3.

Kapitza, C., "Continuous Glucose Monitoring: Reliable Measurements for Up to 4 Days With the SCGMI System", Diabetes Technology & Therapeutics, 2003, p. 609-614, vol. 5, No. 4.

Kovatchev, B. P., "Assessment of Risk for Severe Hypoglycemia Among Adults With IDDM: Validation of the Low Blood Glucose Index", Diabetes Care, 1998, p. 1870-1875, vol. 21, No. 11.

Kovatchev, B. P., "Association of Self Monitoring Blood Glucose Profiles With Glycosylated Hemoglobin in Patients with Insulin-Dependent Diabetes", Methods in Enzymology, 2000, p. 410-417, vol. 321.

Kovatchev, B. P., "Methods for Quantifying Self-Monitoring Blood Glucose Profiles Exemplified by an Examination of Blood Glucose Patterns in Patients With Type 1 and Type 2 Diabetes", Diabetes Technology & Therapeutics, 2002, p. 295-303, vol. 4, No. 3.

Kovatchev, B. P., "Postprandial Symptoms and Cognitive-Motor Function, and Blood Glucose in Type 2 Diabetes Mellitus", Diabetes, Journal of the American Diabetes Association, 2003, p. A416, Supplement 1.

Kovatchev, B. P., "Risk Analysis of Blood Glucose Data: A Quantitative Approach to Optimizing the Control of Insulin Dependent Diabetes", Journal of Theoretical Medicine, 2000, p. 1-10, vol. 3.

Lodwig, V., "Continuous Glucose Monitoring with Glucose Sensors: Calibration and Assessment Criteria", Diabetes Technology & Therapeutics, 2003, p. 573-587, vol. 5, No. 4.

Mastrototaro, J. J., "The Minimed Continuous Glucose Monitoring System", Diabetes Technology & Therapeutics, 2000, p. S13-S18, vol. 2, Supplement 1.

Soonthornpun, S., "Postprandial Plasma Glucose: A Good Index of Glycemic Control in Type 2 Diabetic Patients Having Near-Normal Fasting Glucose Levels", Diabetes Research and Clinical Practice, 1999, p. 23-27, vol. 46, Issue 1.

Food and Drug Administration, "Review Criteria Assessment of Portable Blood Glucose Monitoring in Vitro Diagnostic Devices Using Glucose Oxidase, Dehydrogenase or Hexokinase Methodology", 1997.

Diabetes Control and Complications Trial Research Group, "The Effect of Intensive Treatment of Diabetes on the Development and Progression of Long Term Complications in Insulin-Dependent Diabetes Mellitus", The New England Journal of Medicine, 1993, p. 977-986, vol. 329, No. 14.

"Intensive Blood-Glucose Control with Sulphonylureas or Insulin Compared with Conventional Treatment and Risk of Complications in Patients with Type 2 Diabetes", UK Prospective Diabetes Study (UKPDS) Group, The Lancet, 1998, p. 837-853, vol. 352.

* cited by examiner

| | | Point Error-Grid Zones | | | | | | | | | |
|---|---|---|---|---|---|---|---|---|---|---|---|
| | | Hypoglycemia BG < 70 mg/dl | | | Euglycemia 70<BG<180mg/dl | | | Hyperglycemia BG > 180 mg/dl | | | |
| | | A | D | E | A | B | C | A | B | C | D | E |
| Rate Error- Grid Zones | A | 60% | 10% | 3% | 60% | 13% | 0% | 60% | 8% | 3% | 3% | 0% |
| | B | 10% | 5% | 2% | 12% | 5% | 0% | 7% | 5% | 2% | 2% | 0% |
| | uC | 3% | 1% | 0% | 4% | 1% | 0% | 2% | 1% | 0% | 0% | 0% |
| | lC | 2% | 1% | 0% | 1% | 1% | 0% | 3% | 1% | 0% | 0% | 0% |
| | uD | 1% | 1% | 0% | 1% | 0% | 0% | 1% | 1% | 0% | 0% | 0% |
| | lD | 1% | 0% | 0% | 0% | 1% | 0% | 0% | 0% | 0% | 0% | 0% |
| | uE | 0% | 0% | 0% | 0% | 0% | 0% | 0% | 0% | 0% | 0% | 0% |
| | lE | 0% | 0% | 0% | 0% | 0% | 0% | 0% | 0% | 0% | 0% | 0% |

☐ Accurate Readings  ▨ Benign Errors  ▦ Erroneous Readings

CG-EGA Summary

Combined weighted accuracy across the entire blood glucose range with fixed weights of 0.07, 0.53, and 0.4 for hypoglycemia, euglycemia, and hyperglycemia, respectively:

$A = 84.6\%$
$B = 9.3\%$
$Err = 6.1\%$

Euglycemia (70<BG<=180 mg/dl)
Accuracy = 90%
Point Error-Grid Zones

| Rate Error-Grid Zones | A | B | C |
|---|---|---|---|
| A | 60% | 13% | 0% |
| B | 12% | 5% | 0% |
| uC | 4% | 1% | 0% |
| lC | 1% | 1% | 0% |
| uD | 1% | 0% | 0% |
| lD | 1% | 1% | 0% |
| uE | 0% | 0% | 0% |
| lE | 0% | 0% | 0% |

This range contains 53% of the data

Hypoglycemia (BG<=70 mg/dl)
Accuracy = 70%
Point Error-Grid Zones

| Rate Error-Grid Zones | A | D | E |
|---|---|---|---|
| A | 60% | 10% | 3% |
| B | 10% | 5% | 2% |
| uC | 3% | 1% | 0% |
| lC | 2% | 1% | 0% |
| uD | 1% | 1% | 0% |
| lD | 1% | 0% | 0% |
| uE | 0% | 0% | 0% |
| lE | 0% | 0% | 0% |

This range contains 7% of the data

Hyperglycemia (BG > 180 mg/dl)
Accuracy = 80%
Point Error-Grid Zones

| | A | B | C | D | E |
|---|---|---|---|---|---|
| A | 60% | 8% | 3% | 3% | 0% |
| B | 7% | 5% | 2% | 2% | 0% |
| uC | 2% | 1% | 0% | 0% | 0% |
| lC | 3% | 1% | 0% | 0% | 0% |
| uD | 1% | 1% | 0% | 0% | 0% |
| lD | 1% | 0% | 0% | 0% | 0% |
| uE | 0% | 0% | 0% | 0% | 0% |
| lE | 0% | 0% | 0% | 0% | 0% |

This range contains 40% of the data

LEGEND
Zone A – Clinically accurate;
Zone B – Benign Rx;
Zone C – Over corrective Rx;
Zone D – Failure to Detect;
Zone E – Erroneous Rx.

FIG. 8

METHOD, SYSTEM AND COMPUTER PROGRAM PRODUCT FOR EVALUATING THE ACCURACY OF BLOOD GLUCOSE MONITORING SENSORS/DEVICES

CROSS-REFERENCES TO RELATED APPLICATIONS

This application is a national stage filing of International Application No. PCT/US2005/013792 filed on Apr. 21, 2005, which claims priority under 35 U.S.C. §119(e) from U.S. Provisional Patent Application Ser. No. 60/564,195, filed Apr. 21, 2004, entitled "Continuous Glucose Error-Grid Analysis (CG-EGA): A Method, System and Computer Program Product for Evaluating the Accuracy of Continuous Blood Glucose Monitoring Sensors," the disclosures of which are hereby incorporated by reference herein in their entirety.

FIELD OF THE INVENTION

The present invention relates to the method and related system for evaluating the accuracy of a glucose monitoring sensors or instruments, in particular continuous or semi-continuous glucose sensors or instruments and related methods.

BACKGROUND OF THE INVENTION

In the Diabetes Control and Complication Trial (DCCT) (1), the risks of microvascular (retinopathy and nephropathy) and neuropathic complications of diabetes were predicted by Hemoglobin A1c (HbA1c) for subjects with Type 1 diabetes (T1 DM). Similarly, for those with Type 2 diabetes (T2DM), in the United Kingdom Prospective Diabetes Study (UKPDS) the risks of microvascular complications of diabetes were predicted based on HbA1c (2). However, blood glucose (BG) fluctuations are a process in time and understanding their temporal characteristics is important. Despite the excellent predictive power of HbA1c for chronic diabetes complications, patients commonly experience disturbing symptoms related to rapid blood glucose (BG) swings deviating from their average glycemia. Measures of average glycemia thus may fail to capture important aspects of the temporal patterns of glycemia (3). Recently, it has been reported that extreme fluctuations in glucose values are important markers of diabetes control in both T1DM and T2DM (4): (i) the Low BG Index (LBGI) (5, 6) predicts the risk and frequency of severe hypoglycemia; (ii) the High BG Index (HBGI) predicts the risk of extremes of hyperglycemia (5, 7), and (iii) previously reported symptom-BG associations (8) and recent data (9) suggest that BG rate of change may be linked to the development of negative mood and cognitive symptoms, especially post meals (9). Mounting evidence point to the importance of rapid BG fluctuations for long-term diabetes complications as well. A number of recent studies found that postprandial hyperglycemia is an independent factor contributing to cardiovascular complications and increased mortality, especially in T2DM (10, 11, 12, 13, 14, 15). The Diabetes Intervention Study, concluded that postprandial, but not fasting BG, was an independent predictor of mortality in T2DM (15). A recent review of studies in this area concluded that there are now comprehensive and consistent data from pathophysiological as well as epidemiologic studies that excessive post-load glucose excursions have acute and chronic harmful effects on the endothelium and vessel wall (16). Thus, an accurate assessment of BG dynamics in peoples' natural environment is a valuable tool for both everyday maintenance of diabetes and long-term effectiveness of glycemic control. This is the premise behind increasing industrial and research efforts concentrated on the development of sensors for continuous, or nearly continuous, monitoring of BG (CGS, 17, 18, 19). Compared to a few self-monitoring BG (SMBG) readings per day, continuous glucose sensor (CGS) yield detailed time series of BG determinations, e.g. BG samples every 5 minutes for several days. The evaluation of the accuracy of CGS, however, is not straightforward, especially if taken in the context of established accuracy measures, such as statistical correlation or regression, or the clinically based Error-Grid Analysis (EGA) previously introduced (20, 21). A problem is that all these accuracy measures are designed to reflect the quality of approximation of reference BG by measurements taken in isolated static points in time, regardless of the temporal structure of the data. As such, these measures work well for evaluation of self-monitoring (SMBG) devices and are accepted by FDA as valid supplements to the review of clinical measurement methods (22, 23). However, applying these measures to evaluate the process approximation offered by CGS is questionable. An analogy of CGS vs. SMBG with camcorders vs. still cameras is inevitable, and might be helpful. Still cameras produce highly accurate snapshots of a process in time; camcorders generally offer lower resolution and precision of each separate image, but capture the dynamics of the action. Thus, it would be inappropriate to gauge the accuracy of still cameras and camcorders using the same static measure—the number of pixels in a single image. Similarly, it is inappropriate to gauge the precision of CGS and SMBG devices using the same measures, especially when these measures ignore the temporal characteristics of the observed process.

The original Error Grid Analysis (EGA) some time ago, which was intended to quantify the clinical significance of the agreement between a BG estimate and reference value (20). While other methods were available to quantify the statistical significance of such agreement, such as correlational and regression analyses, these approaches did not address the important question of the clinical implications of accuracy of BG estimates, i.e., what would be the potential outcome if a patient took some self-treatment action based upon a BG estimate. In its original form, the EGA was used to quantify the accuracy of patient BG estimates, based on physical symptoms and information about time of day, insulin, food and physical activity, compared to BG meter values. Subsequently, the EGA was used to assess the accuracy of BG meters compared to reference laboratory measurements (21). Over time, the EGA became one of the accepted standards for demonstrating acceptable levels of accuracy of BG meters to the FDA (23).

The original EGA plots each BG estimate (from any source) on the Y-axis against its companion reference BG measure on the X-axis, so that each estimate falls into one of 10 zones (upper and lower A-E zones). The upper and lower A zones are clinically accurate, indicating that a BG estimate deviates less than 20% from the reference, or that both the estimate and reference value are <70 mg/dl. These estimates are considered accurate because they are likely to lead to an appropriate clinical response (e.g., attempting to raise a BG value that is too low or lower a BG value that is too high). Clinically significant errors are those that fall into the upper and lower 1) C zones (possible over-correction when estimated BG indicates treatment may be needed but reference value is in an acceptable range), 2) D zones (failure to detect and possibly treat reference BG levels that are too low or too high, and 3) E zones (erroneous estimates indicating that BG needs to be raised when it is actually too high already, and vice versa). Estimates falling into the remaining area of the Error Grid are B zone errors, indicating benign errors that deviate more than 20% from the reference value but are unlikely to lead to any clinical action or have significant implications if action is taken.

Once the original EGA was published, the scientific community quickly recognized the important unique information provided by this method of evaluating accuracy, and it became a standard component of almost all clinical trials of new BG meters. This was an appropriate use of the EGA since BG meters are designed to provide an accurate estimate of a single static BG value. However, because the EGA only quantifies point accuracy of each single static estimate of BG, and does not take into consideration temporal characteristics of BG fluctuations, its use for determining the accuracy of CGS devices is problematic. In fact, because the EGA does not quantify the accuracy of estimations of temporal changes, such as rate and direction of BG fluctuation, it may even yield misleading results concerning the clinical implications of errors in CGS devices.

Traditional device evaluation methods fail to capture a most important temporal characteristic of the continuous glucose monitoring process.

BRIEF SUMMARY OF INVENTION

Various embodiments of the present invention comprises, but not limited thereto, a Continuous Glucose Error-Grid Analysis (CG-EGA) method, system or computer program product designed for evaluation of continuous glucose sensors providing frequent (e.g., every 5 minutes or desired/required period or frequency) BG readings. CG-EGA estimates the precision of such sensors/devices in terms of both BG values and temporal characteristics of BG fluctuation. The estimates are then combined in a single accuracy assessment that preserves the clinical assumptions of our original EGA (21, 24). This "backward compatibility" makes the accuracy evaluation of continuous glucose sensors using the present invention CG-EGA comparable to accuracy evaluation of SMBG devices using the traditional EGA.

The various embodiments of the present invention Continuous Glucose Error-Grid Analysis (CG-EGA) provides, for example, a new method, system, and computer program product for evaluating the accuracy of continuous glucose monitoring sensors in terms of both accurate blood glucose (BG) values, and accurate direction and rate of BG fluctuations. It should be appreciated that continuous glucose sensors allow, for the first time, routine observation of BG fluctuations as a process in time. The various embodiments of the present invention, account for, among other things, specifics of process characterization (location, speed and direction), and for biological limitations of the observed processes (time lags associated with interstitial sensors).

An embodiment of the present invention CG-EGA includes two interacting components: (1) Rate Error-Grid Analysis assessing sensors' ability to capture the direction and rate of BG fluctuations, and (2) Point Error-Grid Analysis evaluating the sensors' point accuracy in terms of correct presentation of BG values. The CG-EGA then combines rate and point accuracy in a single estimate of sensor precision using a weighed combination of three grids designed specifically for hypoglycemic, euglycemic, and hyperglycemic BG ranges.

An aspect of an embodiment of the present invention is directed to a method for evaluating accuracy of a glucose monitoring sensor. The method comprising: evaluating point accuracy of blood glucose (BG) values received from the monitoring sensor; evaluating accuracy of direction and rate of BG fluctuations received from the monitoring sensor; and combining the point accuracy and rate accuracy in an estimate of sensor precision. The accuracy evaluation of direction and rate of BG fluctuations includes performing rate error-grid analysis (R-EGA), and the accuracy evaluation blood glucose (BG) values includes performing point error-grid analysis (P-EGA) that determines correct presentation of the blood glucose (BG) values. The method may further comprise: splitting the reference BG values received from a reference sensor BG monitoring device into three clinically meaningful regions including hypoglycemia, euglycemia and hyperglycemia regions; and combining results from the rate error-grid analysis (R-EGA) and point error-grid analysis (P-EGA) within each of these regions.

Another aspect of an embodiment of the present invention is directed to a system for evaluating accuracy of a glucose monitoring sensor. The system may comprise a microprocessor or the like programmed to perform the following: evaluate point accuracy of blood glucose (BG) values received from the monitoring sensor; evaluate accuracy of direction and rate of BG fluctuations received from the monitoring sensor; and combine the point accuracy and rate accuracy in an estimate of sensor precision.

Additionally, an aspect of an embodiment of the present invention is directed to a computer program product comprising a computer usable medium having computer program logic for enabling at least one processor in a computer system to evaluate accuracy of a glucose monitoring sensor. The computer program logic may comprise: evaluating point accuracy of blood glucose (BG) values received from the monitoring sensor; evaluating accuracy of direction and rate of BG fluctuations received from the monitoring sensor; and combining the point accuracy and rate accuracy in an estimate of sensor precision.

Further yet, an aspect of an embodiment of the present invention is directed to a system for evaluating accuracy of a glucose monitoring sensor. The system comprises a glucose monitoring sensor and a microprocessor. The microprocessor may be programmed to perform the following: evaluate point accuracy of blood glucose (BG) values received from the monitoring sensor; evaluate accuracy of direction and rate of BG fluctuations received from the monitoring sensor; and combine the point accuracy and rate accuracy in an estimate of sensor precision.

Further still, an aspect of an embodiment of the present invention is directed to a system for evaluating accuracy of a glucose monitoring sensor. The system comprises a glucose monitoring sensor, a reference device; and a microprocessor. The microprocessor being programmed to perform the following: evaluate point accuracy of blood glucose (BG) values received from the monitoring sensor; evaluate accuracy of direction and rate of BG fluctuations received from the monitoring sensor; and combine the point accuracy and rate accuracy in an estimate of sensor precision.

These and other objects, along with advantages and features of the invention disclosed herein, will be made more apparent from the description, drawings and claims that follow.

BRIEF SUMMARY OF THE DRAWINGS

The foregoing and other objects, features, and advantages of the present invention, as well as the invention itself, will be more fully understood from the following description of the invention, when read together with the accompanying drawings, in which:

FIG. 4 provides a grid that combines rate and point error-grid zones with possible R-EGA (rows) and P-EGA (columns) values.

FIGS. 7-8 provide a graphic illustration of an exemplary meter evaluation that may provided in a print out form, computer/PDA monitor form, or data storage medium, for example.

DETAILED DESCRIPTION OF THE INVENTION

Figure 1:
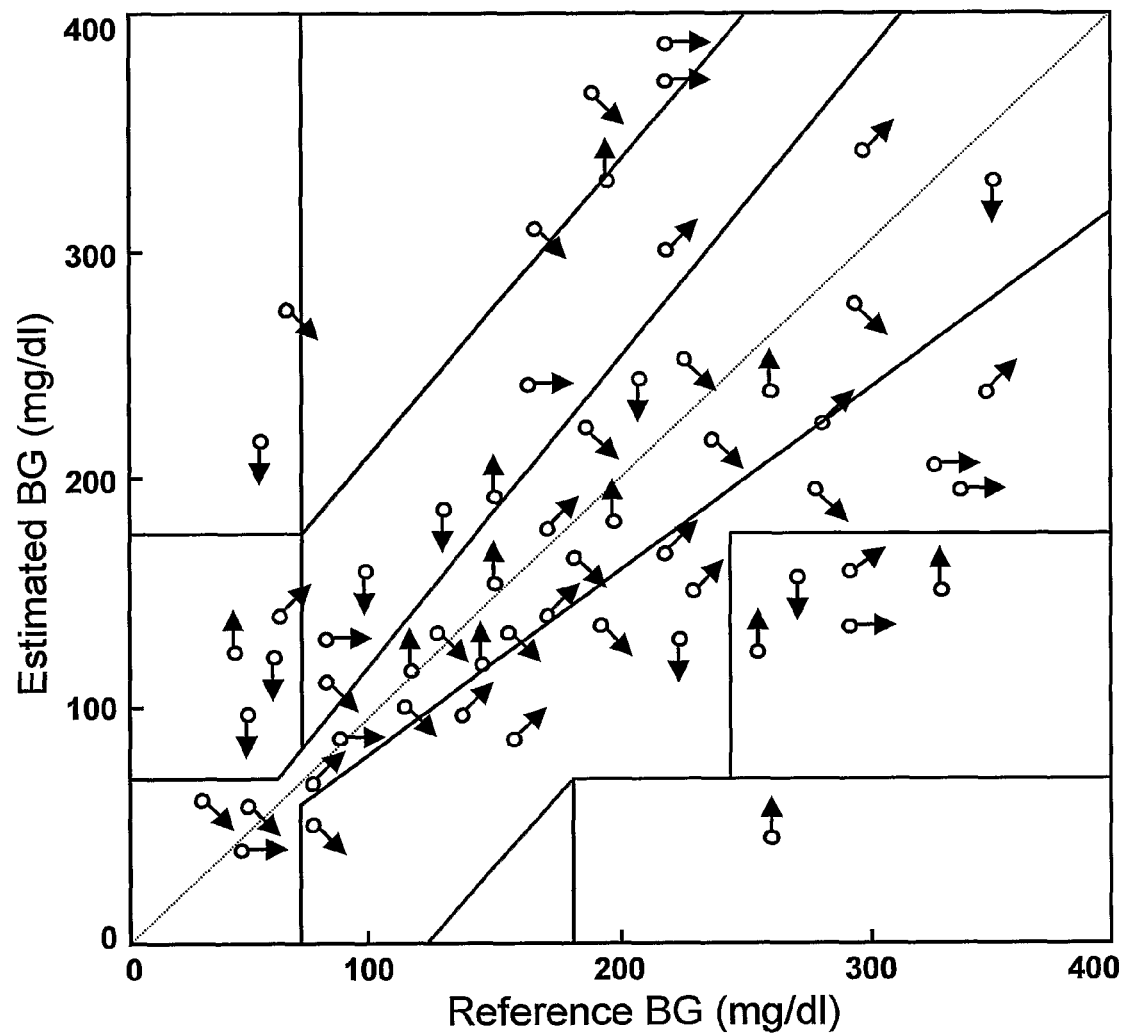
FIG. 1 provides a vector presentation of sensor (estimated) vs. reference BG over the grid of the traditional EGA.

BG fluctuations are a continuous process in time BG(t), and each point of that process is characterized by its location, speed, and direction of change. In other words, at any point in time BG(t) is a vector with a specific bearing. Turning to FIG. 1, FIG. 1 presents such vectors depicted over the grid of the traditional EGA. The exemplary vectors are illustrated on the grid with circles having arrow heads.

CGS allows monitoring this process in short (e.g. 5-min) increments, in essence producing a parallel discrete time series that approximates BG(t). It should be appreciated that the increments may be any desired or required time period, interval or frequency. The periods may be equivalent or varied. Thus, CG-EGA has to judge the precision of this process approximation in terms of both accuracy of BG readings, and accuracy of evaluation of the direction of BG change. Consequently, a Point Error-Grid Analysis (P-EGA) and Rate Error-Grid Analysis (R-EGA) is introduced that deal with these two requirements.

In an embodiment, in order to construct R-EGA and P-EGA it is set forth that paired reference-sensor BG readings are available through a sufficiently frequent sampling (e.g. 5-15 minutes) capable of capturing a representative picture of BG fluctuations. It should be appreciated that the frequent sampling period may be less than five minutes or greater than 15 minutes.

An embodiment of the process of sensor evaluation includes the following three steps: 1) computing Rate Error-Grid zones, 2) computing Point Error-Grid zones, and 3) combining Rate and Point Error-Grid zones in a single sensor accuracy assessment.

Rate Error-Grid Analysis (R-EGA)

For each pair of reference BG points $RBG(t_1)$, $RBG(t_2)$ taken at times $t_1$ and $t_2$ reference BG rate is estimated as the ratio of the change in BG divided by the length of the elapsed time interval:

Reference $BG$ Rate of Change (mg/dl/min)=($RBG$($t_2$)−$RBG$($t_1$))/($t_2$−$t_1$).

Similarly, for each pair of sensor reported BG points $SBG(t_1)$, $SBG(t_2)$ taken at times $t_1$ and $t_2$, sensor BG rate is estimated as:

Sensor $BG$ Rate of Change (mg/dl/min)=($SBG$($t_2$)−$SBG$($t_1$))/($t_2$−$t_1$).

Figure 2:
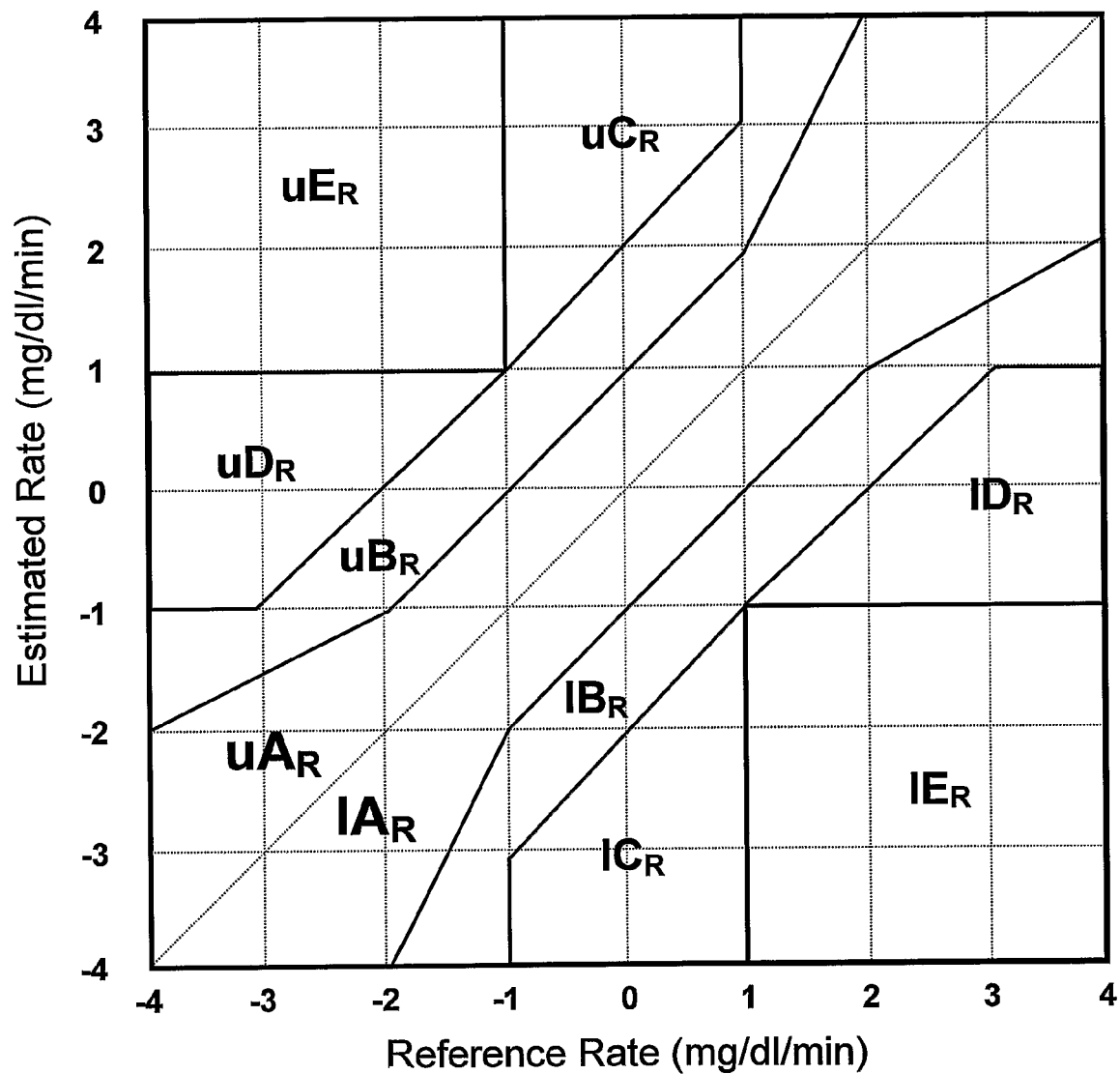
FIG. 2 provides the rate error-grid analysis (R-EGA), wherein the sensor (estimated) BG rate of change is plotted against reference BG rate of change.

Turning to FIG. 2, the sensor (estimated) BG rate of change is then plotted against reference BG rate of change. The boundaries of the scatterplot are set to [−4, 4] mg/dl/min. This assumption follows from evaluation of the observed BG rate of change in 31,000 CGS data points showing that over 99% of all observed changes have rates between −4 and 4 mg/dl/min.

Further, the scatterplot is divided into A through E accuracy zones, which have a clinical meaning similar to the clinical meaning of the original EGA (20, 21, 24). The assumptions behind the zone definition are as follows:

(1) Accurate $A_R$-zone (suffix R stands for rate): The main diagonal in FIG. 2 signifies a perfect fit. A sensor BG rate of change within 1 mg/dl/min from the main diagonal is considered accurate. The accuracy boundaries are expanded to ±2 mg/dl/min at extreme BG rates of ±4 mg/dl/min because such rapid rates of change is rare, cannot be sustained for prolonged periods, and the correct recognition of their direction is sufficient for an accurate clinical decision.

(2) $C_R$-zone (over-correction): Reference rate is within [−1,1] mg/dl/min showing no significant BG fluctuation. However, the sensor displays a significant BG fluctuation, which could lead to over-treatment. The $C_R$-zone is divided into overestimation (u$C_R$—Upper $C_R$) and underestimation (l$C_R$—Lower $C_R$) of the reference rate of change.

(3) $D_R$-zone (failure to detect): Reference BG shows significant change, while the sensor fails to detect that change showing readings within [−1,1] mg/dl/min. An embodiment can distinguish upper u$D_R$ and lower l$D_R$ zones signifying failure to detect rapid BG fall, or rise, respectively.

(4) $E_R$-zone (erroneous reading)—the sensor display readings that are opposite to the reference rate of change, upper u$E_R$—an actual BG decline is estimated as BG rise, lower l$E_R$—an actual BG rise in interpreted as BG fall.

(5) $B_R$-zone (benign errors): sensor errors that do not cause inaccurate clinical interpretation.

The computation of the R-EGA zones for each pair of reference-sensor BG rates of change uses the formulas below. The output of this computation is a zone, coded as follows:

1-uE; 2-uD; 3-uC; 4-uB; 5-uA; 6-lA; 7-lB; 8-lC; 9-lD; 10-lE

X=REFRATE. (Note: Reference BG rate of change as computed above)

Y=SENSRATE. (Note: Sensor BG rate of change as computed above)

IF (Y ge X) RZONE=5.
IF (Y gt (X+1) and X ge 0-2 and X le 1) RZONE=4.
IF (Y gt 0.5 X and X lt 0-2) RZONE=4.
IF (Y gt 2.0 X and X gt 1) RZONE=4.
IF (Y gt (X+2) and X ge 0-1 and X lt 1) RZONE=3.
IF (Y gt (X+2) and X ge 0-3 and X lt 0-1) RZONE=2.
IF (Y gt 0-1 and X lt 0-3) RZONE=2.
IF (Y gt 1 and X lt 0-1) RZONE=1.
IF (Y it X) RZONE=6.
IF (Y it (X−1) and X ge 0-1 and X le 2) RZONE=7.
IF (Y it 2.0 X and X lt 0-1) RZONE=7.
IF (Y it 0.5 X and X gt 2) RZONE=7.

IF (Y lt (X−2) and X ge 0-1 and X le 1) RZONE=8.
IF (Y lt (X−2) and X gt 1 and X le 3) RZONE=9.
IF (Y lt 1 and X gt 3) RZONE=9.
IF (Y lt 0-1 and X gt 1) RZONE=10.

Point Error-Grid Analysis (P-EGA)

Again this analysis is complimentary with traditional EGA, for example (20, 21, 24). As presented in FIG. 3, P-EGA is a scatterplot of sensor vs. reference BG divided into $A_P$, $B_P$, $C_P$, $D_P$, and $E_P$ zones (suffix P stands for point, prefix "u" or "l" stands for upper or lower).

Figure 3A:
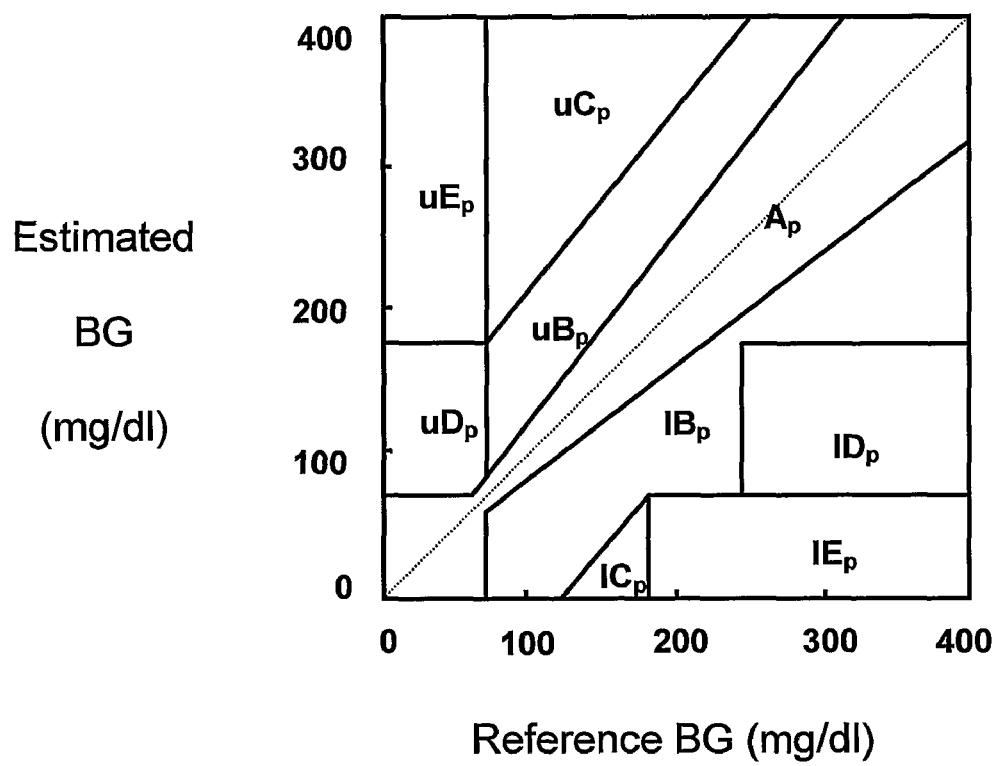
FIGS. 3(A)-(E) provide a point error-grid analysis (P-EGA), wherein P-EGA is a scatterplot of sensor (estimated) vs. reference BG divided into $A_P$, $B_P$, $C_P$, $D_P$, and $E_P$ zones.
Figure 3B:
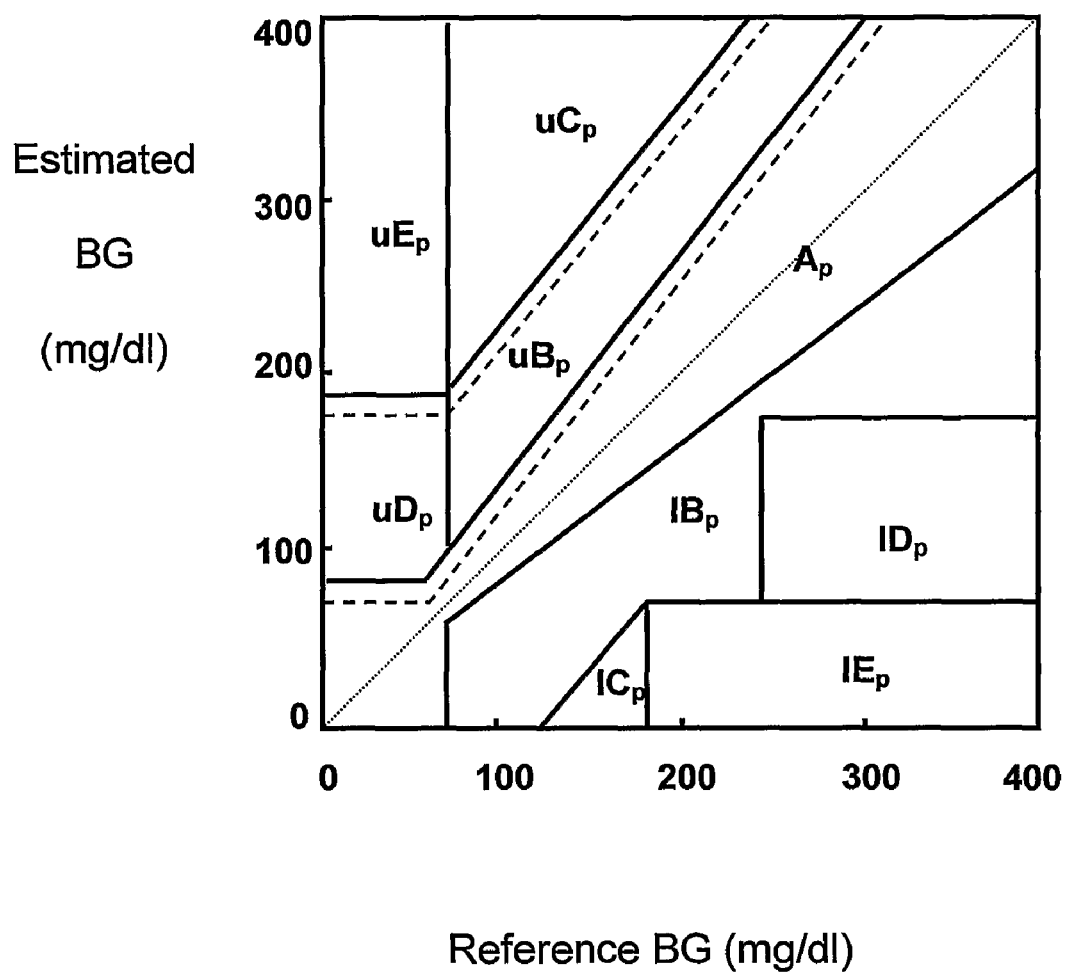
Figure 3C:
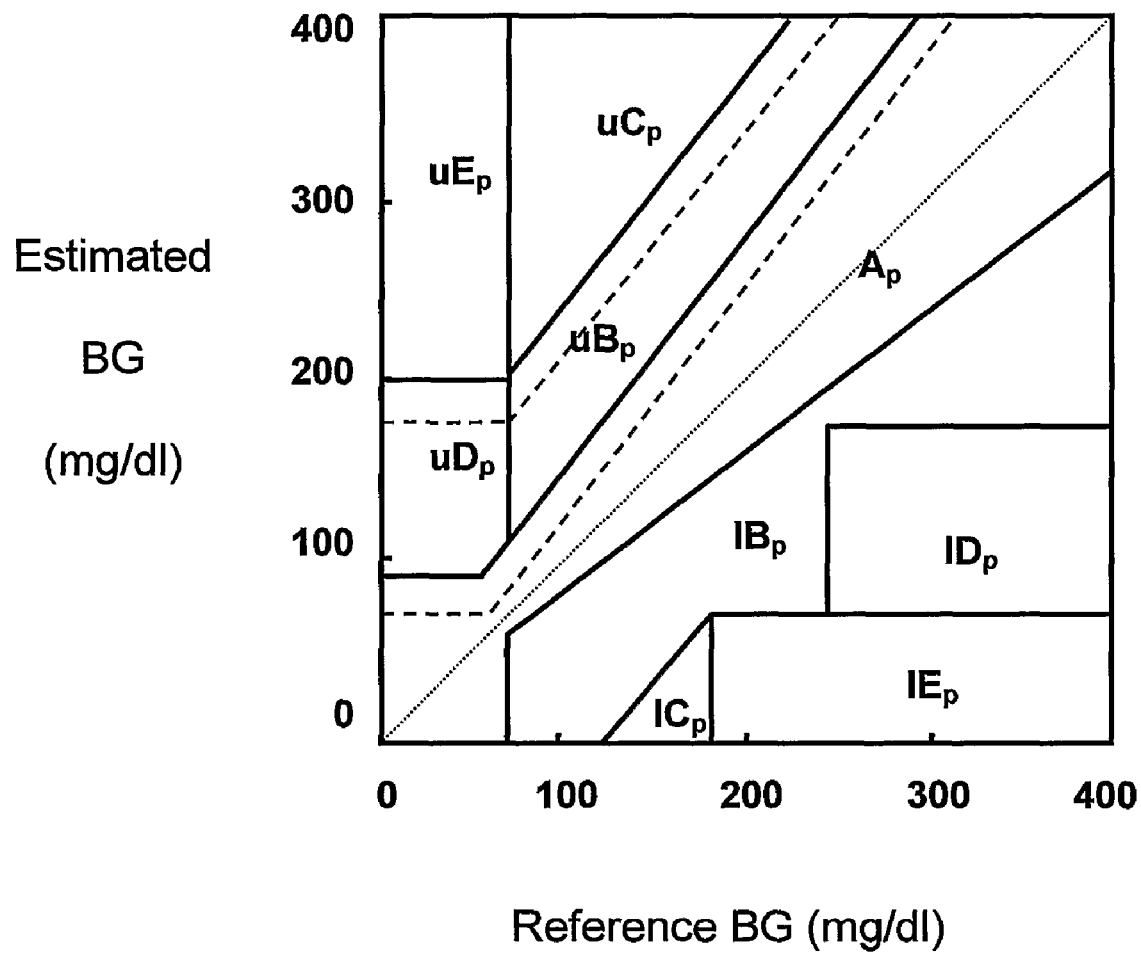
Figure 3D:
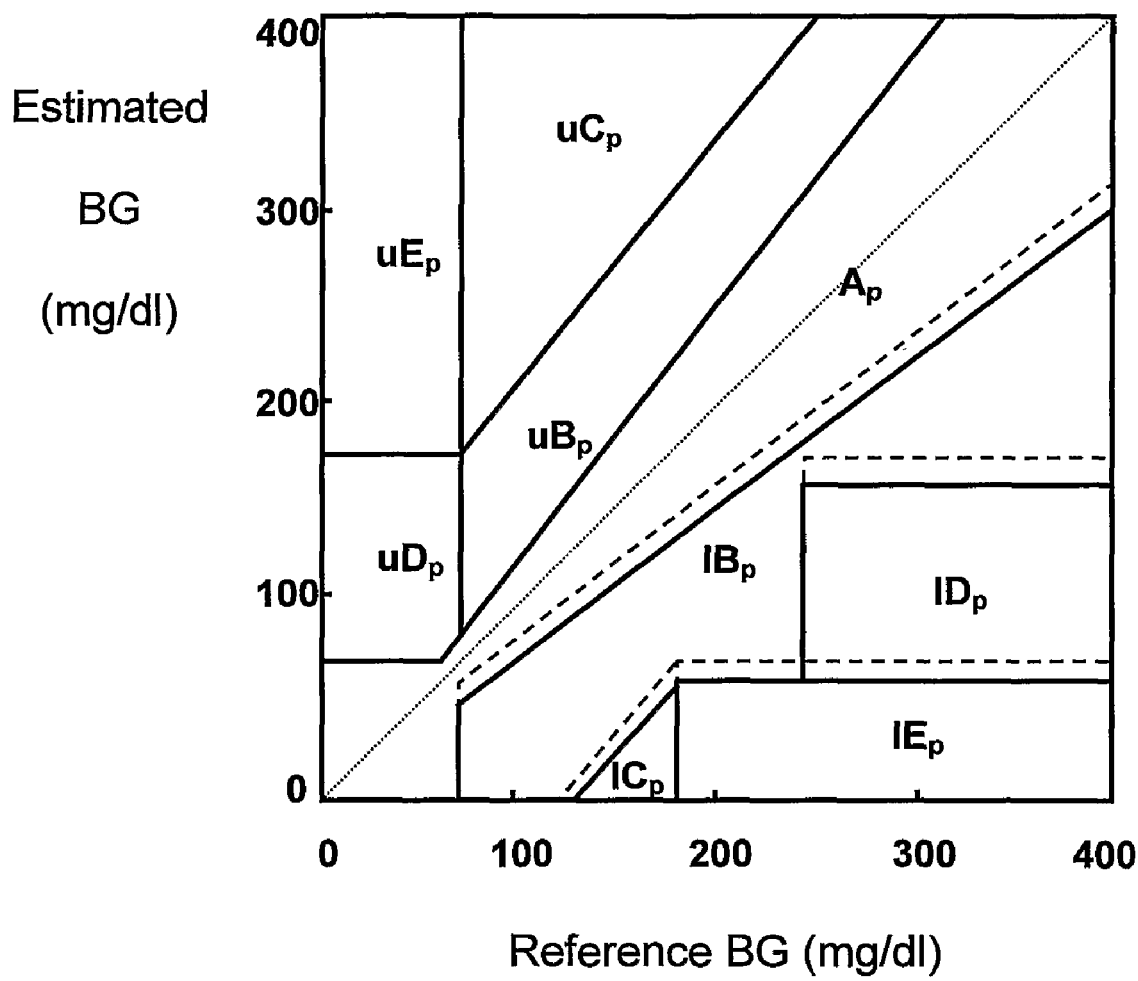
Figure 3E:
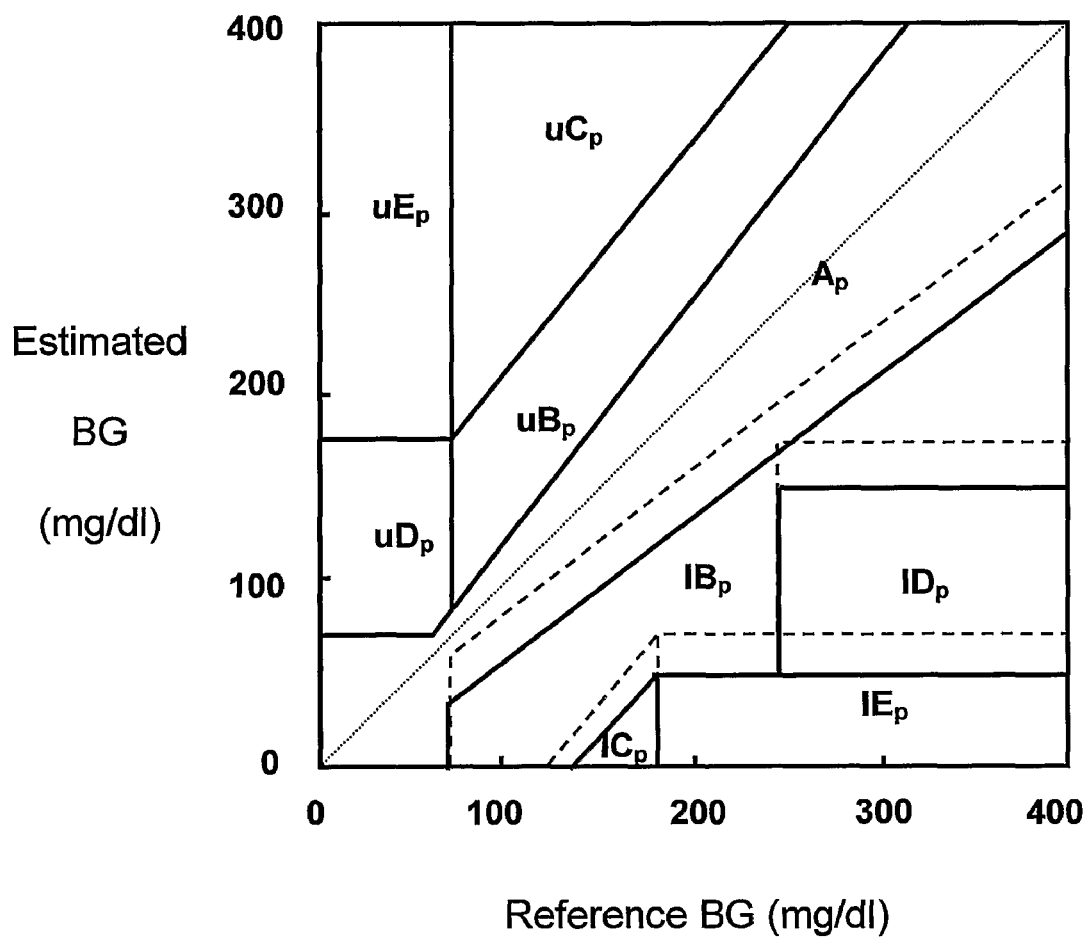

In order to account for the specifics of BG fluctuations interpreted as a process in time, not as separate point readings, these zones are defined depending on the reference rate of BG change as follows:

(1) If the reference BG rate is within [about −1, about 1] mg/dl/min (e.g. no significant change), P-EGA zones are identical to the zones of the traditional EGA, as shown in FIG. 3(A);

(2) If the reference BG is falling at a rate of [about −2, about −1] mg/dl/min, the upper limits of upper $A_P$, $B_P$, and $D_P$ zones are expanded by 10 mg/dl, as shown in FIG. 3(B), wherein the dashed lines are illustrated in $A_P$, $B_P$, and $D_P$ zones;

(3) If the reference BG is falling faster than about −2 mg/dl/min, the upper limits of upper $A_P$, $B_P$, and $D_P$ zones are expanded by 20 mg/dl, as shown in FIG. 3(C), wherein the dashed lines are illustrated in $A_P$, $B_P$, and $D_P$ zones;

(4) If the reference BG is rising at a rate of [about 1, about 2] mg/dl/min, the lower limits of lower $A_P$, $B_P$, and $D_P$ zones are expanded by 10 mg/dl, as shown in FIG. 3(D), wherein the dashed lines are illustrated in lower $A_P$, $B_P$, and $D_P$ zones; and (5) If the reference BG is rising faster than about 2 mg/dl/min, the lower limits of lower $A_P$, $B_P$, and $D_P$ zones are expanded by 20 mg/dl, as shown in FIG. 3(E), wherein the dashed lines are illustrated in lower $A_P$, $B_P$, and $D_P$ zones.

These adjustments are made to equate, in terms of clinical accuracy, the process observation provided by CGS to the point observation provided by SMBG. If BG is rapidly falling and the sensor accurately depicts this descent, then a sensor reading right above the $A_P$ zone will be clinically interpreted as a SMBG reading within the $A_P$ zone. For example, if reference BG is 68 mg/dl and the sensor reads 75 mg/dl and falling at 2 mg/dl/min, the sensor reading will cause a treatment reaction similar to the reference reading. In that sense, the sensor display is clinically accurate (while in the traditional EGA this would be an upper D-zone error). Similarly, when BG is rapidly rising, the lower limits of the lower zones are expanded to accommodate the clinical interpretation of the display. The zone-expansion constants 10 and 20 mg/dl correspond to rates of change 1-2 mg/dl/min, and faster than 2 mg/dl/min. This means that, on average, the sensor reading will reach the corresponding traditional EGA zone within 7 minutes (1.5 mg/dl/min 7 min, or 3 mg/dl/min 7 min). The constant 7 minutes was selected on the basis of reported average delays between blood and interstitial glucose (See Boyne M S, Silver D M, Kaplan J, Saudek C D. Timing of Changes in Interstitial and Venous Blood Glucose Measured With a Continuous Subcutaneous Glucose Sensor. Diabetes 52: 2790-2794, 2003, of which is hereby incorporated by reference herein in its entirety). It should be appreciated that a wide variety of sensor periods may be implemented. In that sense, the zone expansion accounts for time lags inherent to interstitial sensor.

The computation of the P-EGA zones for each pair of reference-sensor BG readings uses the formulas below. The output of this computation is a zone, coded as follows:

1-uE; 2-uD; 3-uC; 4-uB; 5-uA; 6-lA; 7-lB; 8-lC; 9-lD; 10-lE

If the BG rate of change is between −1 and 1 mg/dl/min, use the formulas:
U1=REFBG. (Note: Reference BG)
W1=SENBG. (Note: Sensor BG)
IF (W1 ge U1) ZONE0=5.
IF (W1 ge 1.20 U1 and U1 gt 70) ZONE0=4.
IF (W1 ge (1.03 U1+107.9) and U1 gt 70) ZONE0=3.
IF (W1 ge 1.20 U1 and W1 gt 70 and U1 le 70) ZONE0=2.
IF (W1 ge 180 and U1 le 70) ZONE0=1.
IF (W1 lt U1) ZONE0=6.
IF (W1 le 0.8 U1 and U1 gt 70) ZONE0=7.
IF (W1 le (1.4 U1-182) and U1 le 180) ZONE0=8.
IF (U1 ge 240 and W1 gt 70 and W1 lt 180) ZONE0=9.
IF (U1 gt 180 and W1 le 70) ZONE0=10.

IF BG is falling at a rate of −1 to −2 mg/dl/min use the formulas:
U2=REFBG. (Note: Reference BG)
W2=SENBG. (Note: Sensor BG)
IF (W2 ge U2) ZONE2=5.
IF (W2 ge (1.20 U2+10) and U2 gt 70) ZONE2=4.
IF (W2 ge (1.03 U2+117.9) and U2 gt 70) ZONE2=3.
IF (W2 ge (1.20 U2+10) and W2 gt 80 and U2 le 70) ZONE2=2.
IF (W2 ge 190 and U2 le 70) ZONE2=1.
IF (W2 lt U2) ZONE2=6.
IF (W2 le 0.8 U2 and U2 gt 70) ZONE2=7.
IF (W2 le (1.4 U2-182) and U2 le 180) ZONE2=8.
IF (U2 ge 240 and W2 gt 70 and W2 lt 180) ZONE2=9.
IF (U2 gt 180 and W2 le 70) ZONE2=10.

IF BG is falling faster than −2 mg/dl/min use the formulas:
U4=REFBG. (Note: Reference BG)
W4=SENBG. (Note: Sensor BG)
IF (W4 ge U4) ZONE4=5.
IF (W4 ge (1.20 U4+20) and U4 gt 70) ZONE4=4.
IF (W4 ge (1.03 U4+127.9) and U4 gt 70) ZONE4=3.
IF (W4 ge (1.20 U4+20) and W4 gt 90 and U4 le 70) ZONE4=2.
IF (W4 ge 200 and U4 le 70) ZONE4=1.
IF (W4 lt U4) ZONE4=6.
IF (W4 le 0.8 U4 and U4 gt 70) ZONE4=7.
IF (W4 le (1.4 U4-182) and U4 le 180) ZONE4=8.
IF (U4 ge 240 and W4 gt 70 and W4 lt 180) ZONE4=9.
IF (U4 gt 180 and W4 le 70) ZONE4=10.

IF BG is rising at a rate of 1 to 2 mg/dl/min use the formulas:
U1=REFBG. (Note: Reference BG)
W1=SENBG. (Note: Sensor BG)
IF (W1 ge U1) ZONE1=5.
IF (W1 ge 1.20 U1 and U1 gt 70) ZONE1=4.
IF (W1 ge (1.03 U1+107.9) and U1 gt 70) ZONE1=3.
IF (W1 ge 1.20 U1 and W1 gt 70 and U1 le 70) ZONE1=2.
IF (W1 ge 180 and U1 le 70) ZONE1=1.
IF (W1 lt U1) ZONE1=6.
IF (W1 le (0.8 U1-10) and U1 gt 70) ZONE1=7.
IF (W1 le (1.4 U1-192) and U1 le 180) ZONE1=8.
IF (U1 ge 240 and W1 gt 60 and W1 lt 170) ZONE1=9.
IF (U1 gt 180 and W1 le 60) ZONE1=10.

IF BG is rising faster than 2 mg/dl/min use the formulas:
U3=REFBG. (Note: Reference BG)
W3=SENBG. (Note: Sensor BG)
IF (W3 ge U3) ZONE3=5.
IF (W3 ge 1.20 U3 and U3 gt 70) ZONE3=4.
IF (W3 ge (1.03 U3+107.9) and U3 gt 70) ZONE3=3.
IF (W3 ge 1.20 U3 and W3 gt 70 and U3 le 70) ZONE3=2.
IF (W3 ge 180 and U3 le 70) ZONE3=1.

IF (W3 lt U3) ZONE3=6. U3 gt 70) ZONE3=7.
IF (W3 le (1.4 U3-202) and U3 le 180) ZONE3=8.
IF (U3 ge 240 and W3 gt 50 and W3 lt 160) ZONE3=9.
IF (U3 gt 180 and W3 le 50) ZONE3=10.
IF (W3 le (0.8 U3-20) and Combining Rate and Point Error-Grids The results from R-EGA and P-EGA are combined in a single accuracy assessment depending on the reference BG value of each point. First, reference BG is split into three clinically meaningful regions: hypoglycemia defined as BG<=70 mg/dl (3.9 mmol/l); euglycemia, and hyperglycemia defined as BG>180 mg/dl (10 mmol/l), as shown in the left portion, middle portion and right portion of the table of FIG. 4, respectfully. This division is necessary because different BG levels would require different interpretation of the combination R-EGA+P-EGA. The left portion of the table of FIG. 4 presents a grid of possible R-EGA (rows) and P-EGA (columns) values of a hypothetical sensor in the hypoglycemic range. A reading will be considered accurate if it falls in the $A_P$ zone of P-EGA and in $A_R$ or $B_R$ zones of R-EGA (white squares). The reading is clinically erroneous if it falls in $D_P$ or $E_P$ zones regardless of R-EGA or if it falls in $D_R$ or $E_R$ regardless of P-EGA (vertical hash squares). The rest of the grid squares are considered benign errors (horizontal hash squares).

In other words, the percentage of a sensor's readings within the combined CG-EGA A-zone during hypoglycemia equals the sum of the percentages readings in the two squares ($A_P$, $A_R$) and ($A_P$, $B_R$) in left portion of the table of FIG. 4. In this particular example, during hypoglycemia the sensor has 70% accurate readings, 6% benign errors, and 24% erroneous readings. Similarly, when reference BG is in euglycemic, or hyperglycemic range, the combined rate-point grids are labeled accurate, benign, and erroneous as presented in middle portion of the table of FIG. 4 for euglycemia and right portion of the table of FIG. 4 for hyperglycemia. A premise behind the definition of these combined zones may be for example: to what extent the sensor reading would result in accurate treatment, benign error, or significant error, which includes over-treatment or failure to detect dangerous events. Since the detailed differentiation of C, D, and E-zone errors is usually not utilized in sensor evaluation, in the CG-EGA, these zones are not differentiated.

Finally the results from left, middle and right portions of the table of FIG. 4 are combined in a single accuracy estimate of a sensor using a linear weighted combination.

The formulas combining R_EGA and P-EGA zones are as follows:

$$A(AccurateReadings) = w1*A1 + w2*A2 + w3*A3$$

$$B(BenignErrors) = w1*B1 + w2*B2 + w3*B3$$

$$Err(ErroneousReadings) = w1*Err1 + w2*Err2 + w3*Err3$$

Where A1, B1, Err1 are the percentages of accurate readings, benign errors, and erroneous readings during hypoglycemia; A2, B2, Err2 are the percentages of accurate readings, benign errors, and erroneous readings during euglycemia, and A3, B3, Err3 are the percentages of accurate readings, benign errors, and erroneous readings during hyperglycemia. The weights assigned to the hypoglycemic, euglycemic, and hyperglycemic BG ranges are 0.07, 0.53, and 0.40 respectively. These weights are based on the frequency of occurrence of hypoglycemia and hyperglycemia in the field, computed from 600,000 SMBG data points of 800 subjects with T1DM and T2DM.

In the example given in FIG. 4, the weighted linear combination of all BG ranges results in the following final CG-EGA results:

$$A = 0.07\ 70\% + 0.53\ 90\% + 0.4\ 80\% = 84.6\%$$

$$B = 0.07\ 6\% + 0.53\ 10\% + 0.4\ 9\% = 9.3\%$$

$$Err = 0.07\ 24\% + 0.53\ 0\% + 0.40\ 11\% = 6.1\%$$

Figure 7:
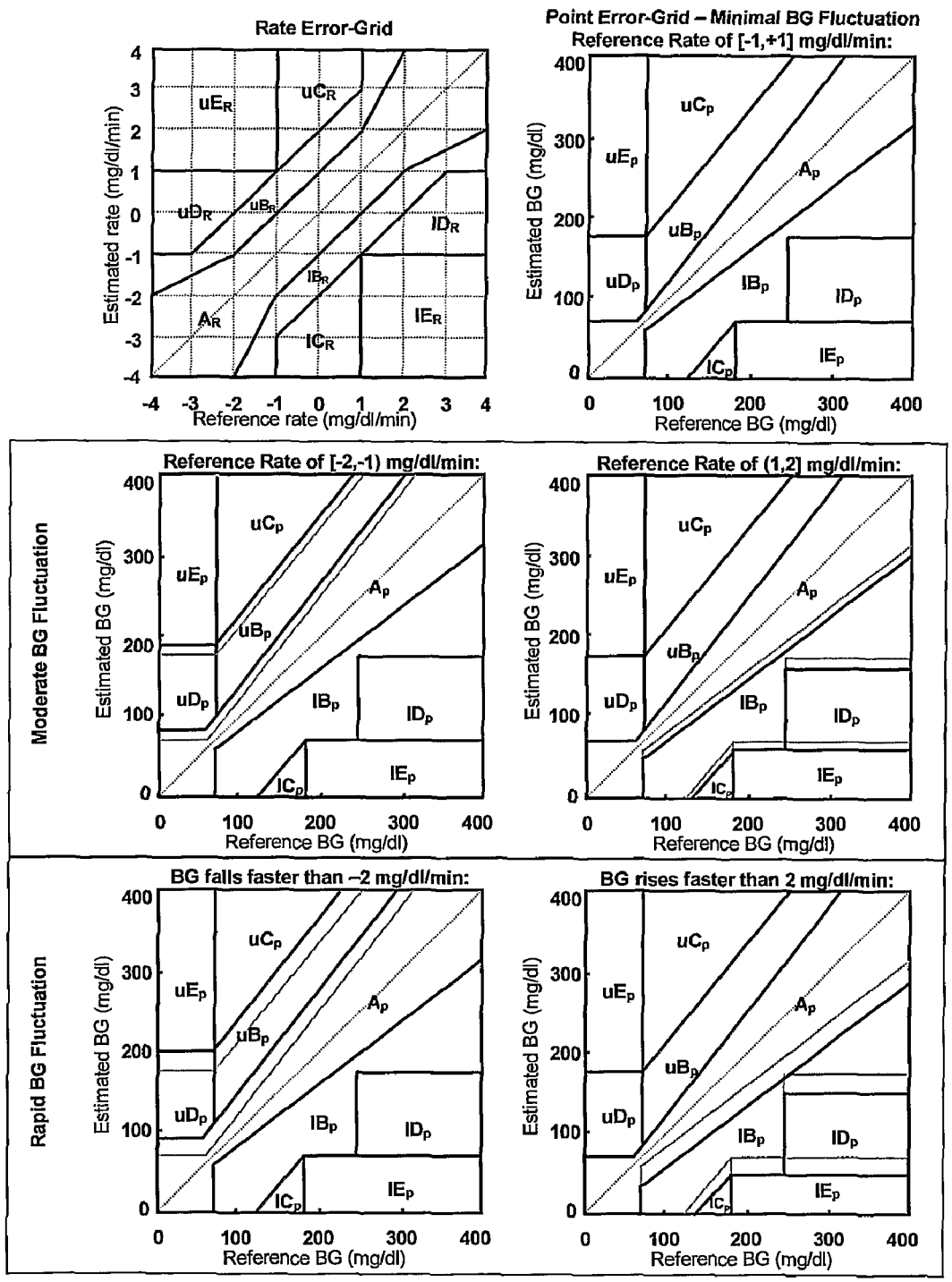

Turning to FIGS. 7 and 8, there is provided a graphic illustration of exemplary Meter Evaluation Sheets that may be provided for a user to review that includes a standardized CGS evaluation sheet presenting visually the results of CG-EGA and as well as in table format the results of CG-EGA. The illustration may be obtained through a printer or computer monitor such as a personal computer or hand held device.

Figure 5:
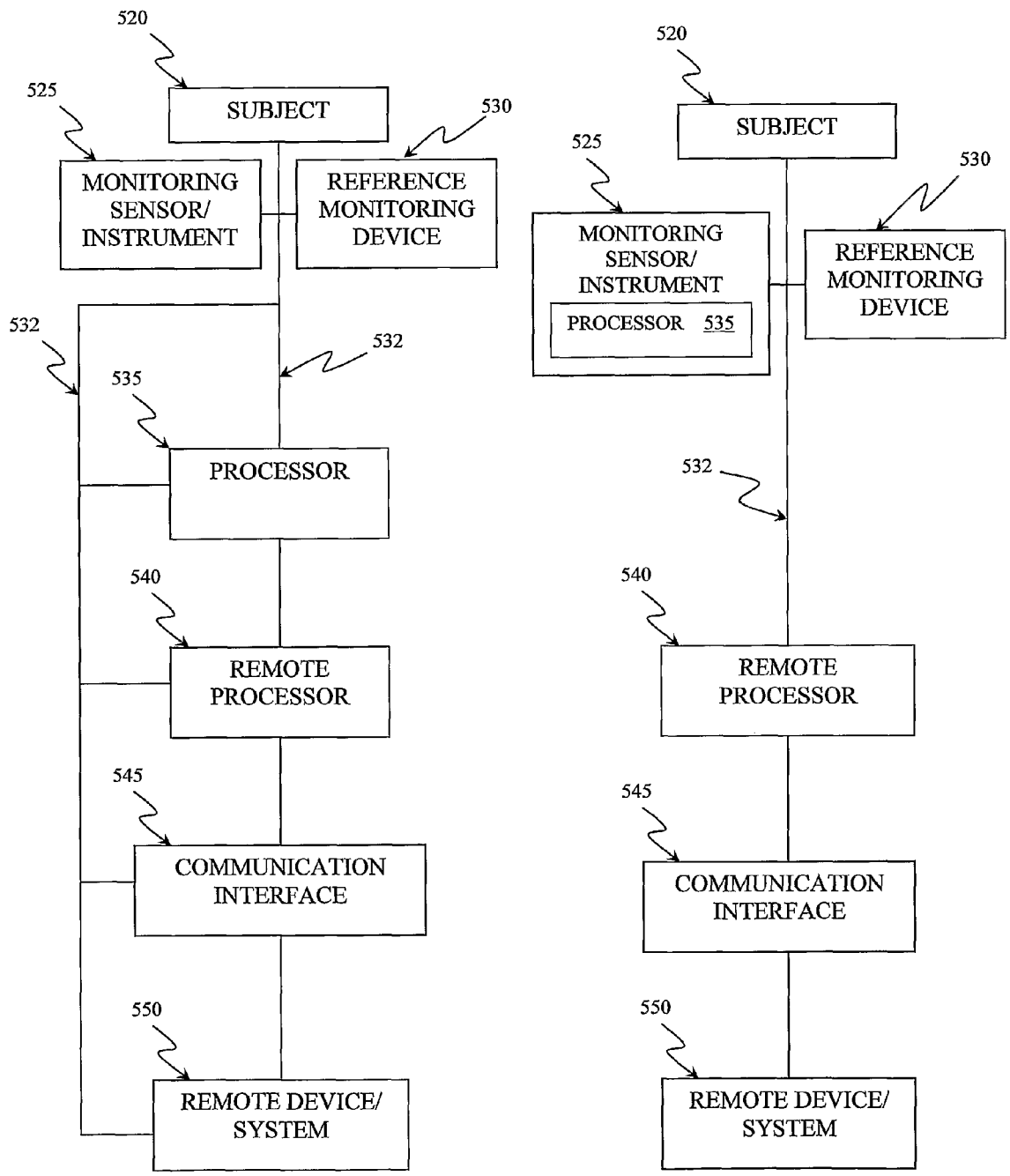
FIGS. 5(A)-(B) are schematic block diagrams of alternative variations of an embodiment of the present invention in communication with related processors, communication interfaces, and systems and/or devices.

FIGS. 5(A)-(B) are schematic block diagrams of alternative variations of an embodiment of the present invention in communication with related processors, communication links, and remote systems, processors, and/or devices. For instance, a continuous (or semi-continuous) monitoring sensor 525 and reference monitoring device 530 receives readings from a subject 520 in accordance with the methodology discussed throughout this document. The subject 520 may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have blood glucose characteristics similar to human (e.g. rat, dog). It should be appreciated that the subject 520 may any applicable patient, for example. A processor 535 in communication with the monitoring sensor 525 and reference monitoring device 530 is adapted to evaluate the accuracy of the continuous (or semi-continuous) monitoring sensor 525 in accordance with the methodologies discussed throughout out this document. The monitoring sensor 525 may be separate from or integral with the processor 535, as shown in FIGS. 5(A)-(B), respectively. Similarly, although not shown, any one or all of the monitoring sensor 525, reference device 530, processor 535 may be separate or integral with one another. Moreover, it should be appreciated that the monitoring sensor 525 and reference device 530 may be in hard-wire or wireless communication with the processor 535. Moreover, any one or all of the monitoring sensor 525, reference device 530, processor 535, may be in communication with (hard wire or wireless) a remote processor 540 communication device 545 and/or remote device 550 via communication path or channel 532. Any part of the communications paths/channels 532 (i.e., communication among the various modules illustrated in FIG. 5 as well as remote modules not specifically illustrated) and related may be implemented using wire or cable, fiber optics, a phone line, a cellular phone link, an RF link, an infrared link, and other physical or wireless communications channels, for example. Additionally, any one or all of the monitoring sensor 525, reference device 530, processor 535, remote processor 540, communication device 545 and/or remote device 550 may be portable such as a PDA, hand held device or lap top or embodied at a work station such at a personal computer or the like. It should be appreciated that any readings received by the subject 520 (or patient) and data handled by the monitoring sensor 525 and reference device 530 may be uploaded via the internet for processing or as desired and sent back to monitoring sensor 525 and reference device 530 or any other location (local or remote) for use, processing or data storage for example.

An example of a remote device 550 may be, for example, a display interface that forwards and provides graphics, text, and other data. Another example of a remote device 550 may be memory, storage drive, or storage medium, such as a floppy disk drive, a magnetic tape drive, an optical disk drive, a flash memory, etc. Examples of a communications interface 545 may include a modem, a network interface (such as an Ethernet card), a communications port (e.g., serial or parallel, etc.), a PCMCIA slot and card, a modem, etc. It should be appreciated that software and data transferred via communications interface or any portion of communication path or channel 532 or the like may be in the form of signals which may be electronic, electromagnetic, optical or other signals capable of being received by communications interface 545 as well as the monitoring sensor 525, reference device 530, processor 535, remote processor 540, communication device 545, and/or remote device/system 550. Other examples of a remote device/system 550 may include at least one of the following: personal computer, processor, keyboard, input device, mouse device, PDA, hand-held device, monitor, printer, work station, remote laboratory, remote medical facility, inpatient facility or system, outpatient facility or system, remote clinic, remote subject or patient site, internet system and intranet system.

It should be appreciated that any or all of the monitoring sensor 525, reference device 530, processor 535, a remote processor 540, communication device 545, remote device/system 550, and communication path or channel 532 may be separately or integrally formed with one another. Moreover, any of these modules/components may be detachable, replaceable, stationary and portable.

Examples of the continuous (or semi-continuous) monitoring sensor 525 and related systems/devices may include, but not limited thereto, the following technologies as discussed in the following U.S. patents and of which are hereby incorporated by reference herein in their entirety:

U.S. Pat. No. 6,865,408 B1 to Abbink et al., entitled "System for Non-Invasive Measurement of Glucose in Humans;"

U.S. Pat. No. 6,853,854 B1 to Proniewicz et al., entitled "Noninvasive Measurement System;"

U.S. Pat. No. 6,675,030 B2 to Ciurczak et al., entitled "Near infrared Blood Glucose Monitoring System;"

U.S. Pat. No. 6,654,620 B2 to Wu et al., entitled "Method for Improving Non-Invasive Determination of the Concentration of Analytes in a Biological Sample;"

U.S. Pat. No. 6,574,501 B2 to Lambert et al., entitled "Assessing Blood Brain Barrier Dynamics or Identifying or Measuring Selected Substances or Toxins in a Subject by Analyzing Raman Spectrum Signals of Selected Regions in the Eye;"

U.S. Pat. No. 6,574,490 B2 to Abbink et al., entitled "System for Non-Invasive Measurement of Glucose in Humans;"

U.S. Pat. No. 6,477,393 B1 to Chou, entitled "Non-Invasive Blood Glucose Measurement Techniques;"

U.S. Pat. No. 6,424,850 B1 to Lambert et al., entitled "Non-Invasive Glucose Monitor;"

U.S. Pat. No. 6,181,957 B1 to Lambert et al., entitled "Non-Invasive Glucose Monitor;"

U.S. Pat. No. 6,097,975 to Petrovsky et al., entitled "Apparatus and Method for Noninvasive Glucose Measurement;" and U.S. Pat. No. 5,077,476 to Rosenthal, entitled "Instrument for Non-Invasive Measurement of Blood Glucose."

Additional examples of the continuous (or semi-continuous) monitoring sensor 525 and related systems/devices may include, but not limited thereto, the following technologies:

CGMS® (CONTINUOUS GLUCOSE MONITORING SYSTEM) by MINIMED MEDTRONIC, Inc.;

GLUCOWATCH® G2™ BIOGRAPHER by CYGNUS/SANKYO PHARMA, Inc.;

GLUCODAY® CONTINUOUS GLUCOSE MONITORING by A. MENARINI DIAGNOSTICS, Inc.;

CONTINUOUS GLUCOSE SENSOR by ANIMAS, Inc.;

FREESTYLE NAVIGATOR CONTINUOUS GLUCOSE MONITOR by THERASENSE, Inc.;

CONTINUOUS GLUCOSE METER by SPECTRX, Inc.;

NIMOS SENSOR by INSTITUT FÜR CHEMO-UND BIOSENSORIK, Inc.;

SYMPHONY™ DIABETES MANAGEMENT SYSTEM by SONTRA MEDICAL:

GLUCONIR by NIR DIAGNOSTICS, Inc.;

SMSI™ GLUCOSE SENSOR by SENSORS FOR MEDICINE AND SCIENCE, Inc.; and

CONTINUOUS GLUCOSE MONITORING SYSTEM by DEXCOM, Inc.

Still yet, other examples of the continuous monitoring sensors and related systems/devices may include, but not limited thereto, the following technologies as discussed in the following references, of which are hereby incorporated by reference herein in their entirety:

1. Diabetes Technol Ther. 2003; 5(4):609-14, "Continuous Glucose Monitoring: Reliable Measurements for Up to 4 Days with the SCGM1 System," Kapitza C, Lodwig V, Obermaier K, Wientjes K J, Hoogenberg K, Junghehn K, Heinemann L; Glucose Monitoring Study Group;

2. Diabetes Technol Ther. 2003; 5(4):572-86, "Continuous Glucose Monitoring with Glucose Sensors: Calibration and Assessment Criteria," Lodwig V, Heinemann L; Glucose Monitoring Study Group; and 3. Diabetes Metab. 2003 April; 29(2 Pt 1): 159-62, "Accuracy of the Continuous Glucose Monitoring System in Inpatient and Outpatient Conditions," Djakoure-Platonoff C, Radermercker R, Reach G, Slama G, Selam J I.

Next, examples of reference monitoring devices 530 and related systems/devices may include, but not limited thereto, the following technologies as discussed in the following U.S. patents, U.S. Applications, or PCT publications and of which are hereby incorporated by reference herein in their entirety:

1. International Patent Application No. PCT/US01/09884, filed Mar. 29, 2001, entitled "Method, System, and Computer Program Product for the Evaluation of Glycemic Control in Diabetes from Self-monitoring Data," and corresponding U.S. patent application Ser. No. 10/240,228, filed Sep. 26, 2002, entitled "Method, System, and Computer Program Product for the Evaluation of Glycemic Control in Diabetes from Self-monitoring Data," and are commonly owned with the present Assignee; and 2. International Patent Application No. PCT/US2003/025053, filed Aug. 8, 2003, entitled "Method, System, and Computer Program Product for the Processing of Self-monitoring Glucose (SMBG) Data to Enance Diabetic Self-management," and corresponding U.S. patent application Ser. No. 10/524,094, filed Feb. 9, 2005, entitled "Managing and Processing of Self-monitoring Glucose (SMBG) Data to Enance Diabetic Self-management." and are commonly owned with the present Assignee.

Additional examples of reference monitoring devices 530 and related systems/devices may include, but not limited thereto, the following technologies: Beckman glucose analyzers; glucose oxidase method, YSI Instruments, Yellow Springs, Ohio, and finger stick glucose meters used by professional personnel, as well as patients for example.

Figure 6:
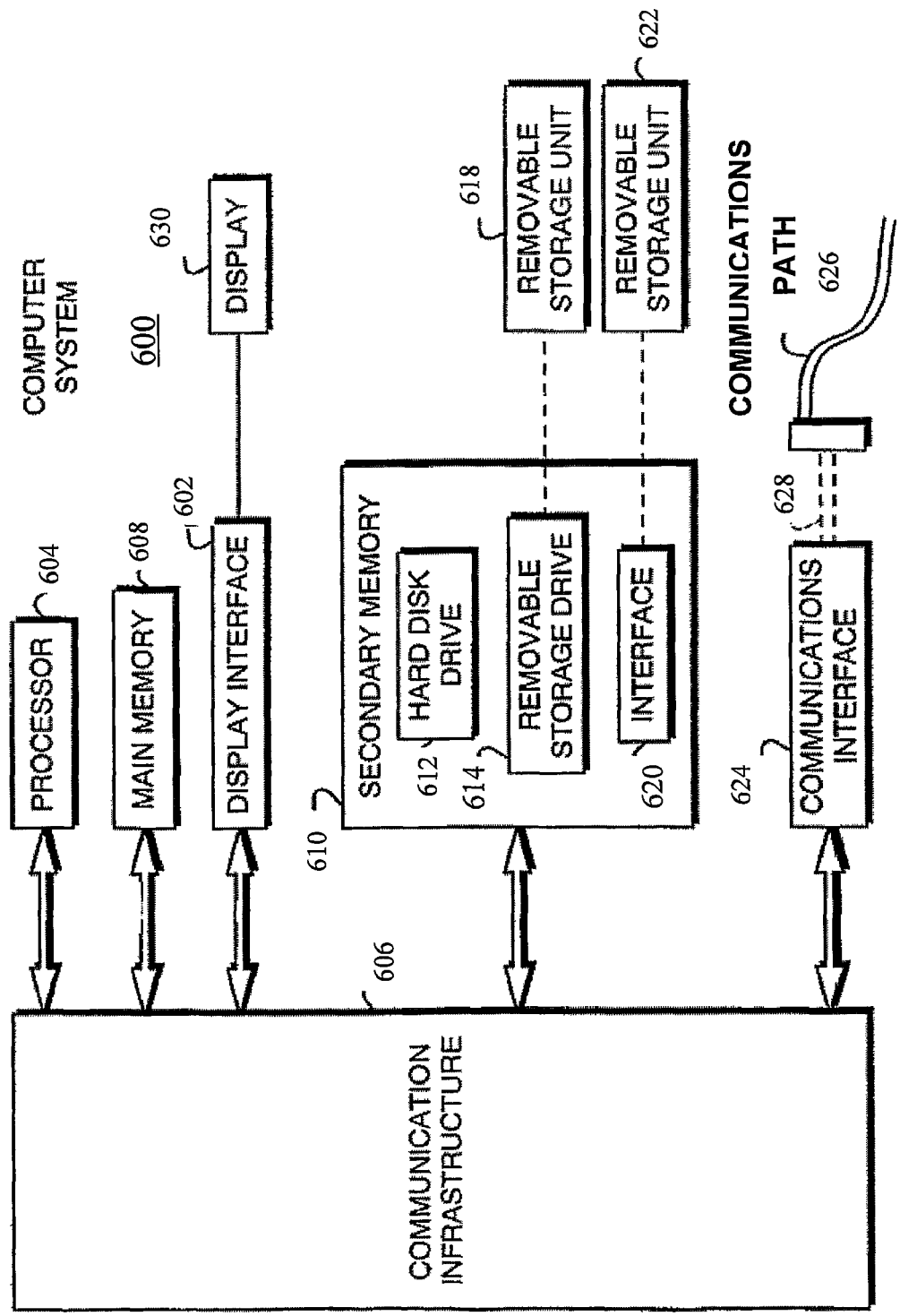
FIG. 6 is a functional block diagram for a computer system for implementation of an exemplary embodiment or portion of an embodiment of present invention.

Turning to FIG. 6, FIG. 6 is a functional block diagram for a computer system for implementation of an exemplary embodiment or portion of an embodiment of present invention. For example, a method of an embodiment of the present invention may be implemented using hardware, software or a combination thereof and may be implemented in one or more computer systems or other processing systems, such as personal digit assistants (PDAs), or directly in a continuous (or semi-continuous) blood glucose monitor or reference glucose monitor. In an example embodiment, an embodiment of the invention was implemented in software running on a general purpose computer 600 as illustrated in FIG. 6. Computer system 600 includes one or more processors, such as processor 604 Processor 604 is connected to a communication infrastructure 606 (e.g., a communications bus, cross-over bar, or network). Computer system 600 may include a display interface 602 that forwards graphics, text, and other data from the communication infrastructure 606 (or from a frame buffer not shown) for display on the display unit 630.

Computer system 600 also includes a main memory 608, preferably random access memory (RAM), and may also include a secondary memory 610. The secondary memory 610 may include, for example, a hard disk drive 612 and/or a removable storage drive 614, representing a floppy disk drive, a magnetic tape drive, an optical disk drive, a flash memory, etc. The removable storage drive 614 reads from and/or writes to a removable storage unit 618 in a well known manner. Removable storage unit 618, represents a floppy disk, magnetic tape, optical disk, etc. which is read by and written to by removable storage drive 614. As will be appreciated, the removable storage unit 618 includes a computer usable storage medium having stored therein computer software and/or data.

In alternative embodiments, secondary memory 610 may include other means for allowing computer programs or other instructions to be loaded into computer system 600. Such means may include, for example, a removable storage unit 622 and an interface 620. Examples of such removable storage units/interfaces include a program cartridge and cartridge interface (such as that found in video game devices), a removable memory chip (such as a ROM, PROM, EPROM or EEPROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between computer system 600 and external devices. Examples of communications interface 624 may include a modem, a network interface (such as an Ethernet card), a communications port (e.g., serial or parallel, etc.), a PCMCIA slot and card, a modem, etc. Software and data transferred via communications interface 624 are in the form of signals 628 which may be electronic, electromagnetic, optical or other signals capable of being received by communications interface 624. Signals 628 are provided to communications interface 624 via a communications path (i.e., channel) 626. Channel 626 carries signals 628 and may be implemented using wire or cable, fiber optics, a phone line, a cellular phone link, an RF link, an infrared link, and other communications channels.

In this document, the terms "computer program medium" and "computer usable medium" are used to generally refer to media such as removable storage drive 614, a hard disk installed in hard disk drive 612, and signals 628. These computer program products are means for providing software to computer system 600. The invention includes such computer program products.

Computer programs (also called computer control logic) are stored in main memory 608 and/or secondary memory 610. Computer programs may also be received via communications interface 624. Such computer programs, when executed, enable computer system 600 to perform the features of the present invention as discussed herein. In particular, the computer programs, when executed, enable processor 604 to perform the functions of the present invention. Accordingly, such computer programs represent controllers of computer system 600.

In an embodiment where the invention is implemented using software, the software may be stored in a computer program product and loaded into computer system 600 using removable storage drive 614, hard drive 612 or communications interface 624. The control logic (software), when executed by the processor 604, causes the processor 604 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in SPSS control language, but could be implemented in other programs such as, but not limited to, C++ programming language or other programs available to those skilled in the art.

In summary, an advantage associated with some of the various embodiments of the present invention includes, but not limited thereto, that this is the first method of evaluation of the clinical accuracy of continuous glucose sensors in terms of both point and rate precision. It should be appreciated that there is rapidly growing number of companies manufacturing devices, including major companies in the diabetes home monitoring market. Each new device, or each device modification, would require numerous evaluations prior to its submission to FDA. Additional evaluations will be required by FDA during their approval process. Typically, after approval a number of research studies and clinical trials involve device accuracy assessment in various patient subgroups or subject patient groups.

Thus, for example, the present invention CG-EGA can become a standard for, among other things, evaluation of the new CGS devices. Moreover, the request for service computing CG-EGA would be significant, and growing. Still yet, the software associate with the present invention may be distributed, or the computation could be provided on-line, such as on-line for-fee service for example.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, material, dimension, time period, or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

The invention may be embodied in other specific forms without departing from the spirit or essential characteristics thereof. The foregoing embodiments are therefore to be considered in all respects illustrative rather than limiting of the invention described herein.

REFERENCES

The following references as cited throughout this document are hereby incorporated by reference herein in their entirety:

1. The Diabetes Control and Complications Trial Research Group: The effect of intensive treatment of diabetes on the development and progression of long-term complications in insulin-dependent diabetes mellitus. *N Engl J Med* 329: 977-986, 1993
2. UK Prospective Diabetes Study (UKPDS) Group: Intensive blood-glucose control with sulphonylureas or insulin compared with conventional treatment and risk of complications in patients with type 2 diabetes. *Lancet*, 352:837-853, 1998
3. Derr R, Garrett E, Stacy G A, Saudek C D: Is HbA1c Affected by Glycemic Instability? *Diab Care* 26: 2728-2733, 2003
4. Kovatchev B P, Cox D J, Gonder-Frederick L A and W L Clarke: Methods for quantifying self-monitoring blood glucose profiles exemplified by an examination of blood glucose patterns in patients with Type 1 and Type 2 Diabetes, *Diabetes Technology and Therapeutics* 4: 295-303, 2002
5. Kovatchev B P, Straume M, Cox D J, Farhy L S. Risk analysis of blood glucose data: A quantitative approach to optimizing the control of insulin dependent diabetes. *J of Theoretical Medicine*, 3:1-10, 2001
6. Kovatchev B P, Cox D J, Gonder-Frederick L A Young-Hyman D, Schlundt D, Clarke W L. Assessment of risk for severe hypoglycemia among adults with IDDM: Validation of the Low Blood Glucose Index, *Diab Care* 21: 1870-1875, 1998
7. Kovatchev B P, Cox D J, Straume M, Farhy L S: Association of Self-monitoring Blood Glucose Profiles with Glycosylated Hemoglobin. In *Methods in Enzymology vol 321: Numerical Computer Methods, Part C*. Johnson & Brand, Eds. New York, Academic Press, 2000, p. 410-417
8. Cox D J, Kovatchev B P, Gonder-Frederick L A, McCall A. Kovatchev B P, Clarke W L. The effects of glucose fluctuation on cognitive function and QOL: the functional costs of hypoglycemia and hyperglycemia among adults with type 1 or type 2 diabetes. *Int J Clin Practice* 129:20-27., 2002
9. Kovatchev B P, Cox D J, Gonder-Frederick L A, Clarke W L, Summers K: Postprandial symptoms and cognitive-motor function, and blood glucose in Type 2 diabetes mellitus. *Diabetes* 52, Supplement 1: A416, 2003
10. Hanefeld M. Temelkova-Kurktschiev T. The postprandial state and the risk of atherosclerosis. *Diabetic Medicine.* 14 Supplement 3: S6-11, 1997.
11. Soonthompun S, Rattarasarn C, Leelawattana R, Setasuban W: Postprandial plasma glucose: a good index of glycemic control in type 2 diabetic patients having near-normal fasting glucose levels. *Diabetes Res Clin Pract* 46: 23-27, 1999.
12. Gavin J R 3rd. The importance of postprandial hyperglycaemia. *International Journal of Clinical Practice. Supplement* (107): 14-17, 1999.
13. Hanefeld M. Post-prandial hyperglycaemia and vascular disease. *International Journal of Clinical Practice. Supplement* (112): 13-18, 2000.
14. Haffner S. The importance of postprandial hyperglycaemia in development of cardiovascular disease in people with diabetes. *International Journal of Clinical Practice. Supplement.* (123): 24-26, 2001.
15. Hanefeld M, Fisher S, Julius U. Risk Factor for myocardial infarction and death in newly detected NIDDM: the Diabetes Intervention Study, 11-year follow-up. *Diabetologia*, 39: 1577-1583, 1996.
16. Hanefeld M. Postprandial hyperglycemia: noxious effects on the vessel wall. *International Journal of Clinical Practice. Supplement* (129): 45-50, 2002.
17. Mastrototaro J J. The MiniMed continuous glucose monitoring system. *Diabetes Technology & Therapeutics*, 2: Supplement 1: S13-S18, 2000.
18. Gross T M, Bode B W, Einhorn D, Kayne D M, Reed J H, White N H, Mastrototaro J J. Performance evaluation of the MiniMed continuous glucose monitoring system during patient home Use. *Diabetes Technology & Therapeutics*, 2000, 2: 49-56.
19. Feldman B, Brazg R, Schwartz S, Weinstein R. A continuous glucose sensor based on wired enzyme technology—results from a 3-day trial in patients with Type 1 diabetes. *Diabetes Technology & Therapeutics*, 2003, 5: 769-778.
20. Cox D J, Clarke W L, Gonder-Frederick L A, Pohl S L, Hoover C, Snyder A, Zimbleman L, Carter W R, Bobbitt S, Pennebaker J. Accuracy of perceiving blood glucose in IDDM, Diabetes Care 8:529-526, 1985.
21. Clarke W L, Cox D J, Gonder-Frederick L A, Carter W R, Pohl SL. Evaluating clinical accuracy of systems for self-monitoring of blood glucose. Diabetes Care 10:622-628, 1987.
22. Food and Drug Administration: Review criteria assessment of portable blood glucose monitoring in vitro diagnostic devices using glucose oxidase, dehydrogenase or hexokinase methodology. Draft guidance document, 1997.
23. Chen E T, Nichols J H, Duh S H, Hortin G. Performance Evaluation of Blood Glucose Monitoring Devices. *Diabetes Technology & Therapeutics*, 2003, 5: 749-768.
24. Cox D J, Gonder-Frederick L A, Kovatchev B P, Julian D M, Clarke W L. Understanding error grid analysis. Diabetes Care 20: 911-912, 1997.

We claim:

1. A method for evaluating accuracy of a glucose monitoring sensor, said method comprising:
   receiving blood glucose (BG) values from said monitoring sensor;
   evaluating accuracy of said BG values received from said monitoring sensor to obtain a point accuracy using a processor;
   receiving BG fluctuations from said monitoring sensor;
   evaluating accuracy of direction and rate of said BG fluctuations received from said monitoring sensor to obtain a rate accuracy using said processor;
   combining said point accuracy and rate accuracy to obtain an estimate of sensor precision using said processor; and
   communicating said estimate of sensor precision to a user using an output device.

2. The method of claim 1, wherein said estimate of sensor precision comprises:
performing a combination of three grids adapted specifically for hypoglycemic, euglycemic, and hyperglycemic BG ranges.

3. The method of claim 2, wherein said estimate of sensor precision includes solely a single estimate using a weighted combination of hypoglycemic, euglycemic, hyperglycemic BG ranges.

4. The method of claim 2, wherein said estimate of sensor precision includes a plurality of estimates using a weighted combination of hypoglycemic, euglycemic, hyperglycemic BG ranges.

5. The method of claim 1, wherein said method is for use with a subject, wherein said subject is a human or an animal.

6. The method of claim 1, wherein said sensor comprises a continuous glucose monitor or semi-continuous glucose monitor or combination of both.

7. The method of claim 1, wherein:
said accuracy evaluation of direction and rate of BG fluctuations includes performing rate error-grid analysis (R-EGA), and
said accuracy evaluation blood glucose (BG) values includes performing point error-grid analysis (P-EGA) that determines correct presentation of said blood glucose (BG) values.

8. The method of claim 7, wherein said estimate of sensor precision comprises:
performing a combination of three grids adapted specifically for hypoglycemic, euglycemic, and hyperglycemic BG ranges.

9. The method of claim 8, wherein said estimate of sensor precision includes solely a single estimate using a weighted combination of hypoglycemic, euglycemic, hyperglycemic BG ranges.

10. The method of claim 8, wherein said estimate of sensor precision includes a plurality of estimates using a weighted combination of hypoglycemic, euglycemic, hyperglycemic BG ranges.

11. The method of claim 7, wherein said method is for use with a subject, wherein said subject is a human or an animal.

12. The method of claim 7, wherein said sensor comprises a continuous glucose monitor or semi-continuous glucose monitor or combination of both.

13. The method of claim 7, wherein said rate error-grid analysis (R-EGA) includes:
for each pair of reference BG points, $RBG(t_1)$ and $RBG(t_2)$, received from a reference blood glucose monitoring device, taken at times $t_1$ and $t_2$, a reference BG rate is estimated as the ratio of the change in the BG points divided by the length of the elapsed time interval as follows:

reference $BG$ rate of change (mg/dl/min)=$(RBG(t_2)-RBG(t_1))/(t_2-t_1)$.

14. The method of claim 13, wherein said rate said error-grid analysis (R-EGA) further includes:
for each pair of sensor reported BG points, $SBG(t_1)$ and $SBG(t_2)$, received from said glucose monitoring sensor, taken at times $t_1$ and $t_2$, a sensor BG rate is estimated as:

sensor $BG$ rate of change (mg/dl/min)=$(SBG(t_2)-SBG(t_1))/(t_2-t_1)$.

15. The method of claim 14, wherein said rate said error-grid analysis (R-EGA) further includes:
scatter plotting said sensor BG rate of change against said reference BG rate of change.

16. The method of claim 15, wherein said rate said error-grid analysis (R-EGA) further includes dividing said scatter plot into accuracy zones.

17. The method of claim 16, wherein said accuracy zones comprise A through E accuracy zones, which have a clinical meaning similar to the clinical meaning of the conventional Error Grid Analysis (EGA).

18. The method of claim 17, wherein said clinical meanings are defined as follows:
(a) AR-zone (accurate);
(b) CR-zone (over-correction);
(c) DR-zone (failure to detect);
(d) ER-zone (erroneous reading); and
(e) BR-zone (benign errors),
wherein suffix R stands for rate.

19. The method of claim 18, wherein said rate error-grid analysis (R-EGA) further includes:
computing said R-EGA zones for each pair of said reference-sensor BG rates of change using the formulas below, wherein X is abbreviated for said reference BG rate of change and wherein Y is abbreviated for said sensor BG rate of change:
IF (Y ge X) RZONE=5,
IF (Y gt (X+1) and X ge 0-2 and X le 1) RZONE=4,
IF (Y gt 0.5× and X lt 0-2) RZONE=4,
IF (Y gt 2.0× and X gt 1) RZONE=4,
IF (Y gt (X+2) and X ge 0-1 and X lt 1) RZONE=3,
IF (Y gt (X+2) and X ge 0-3 and X lt 0-1) RZONE=2,
IF (Y gt 0-1 and X lt 0-3) RZONE=2,
IF (Y gt 1 and X lt 0-1) RZONE=1,
IF (Y lt X) RZONE=6,
IF (Y lt (X−1) and X ge 0-1 and X le 2) RZONE=7,
IF (Y lt 2.0× and X lt 0-1) RZONE=7,
IF (Y lt 0.5× and X gt 2) RZONE=7,
IF (Y lt (X−2) and X ge 0-1 and X le 1) RZONE=8,
IF (Y lt (X-2) and X gt 1 and X le 3) RZONE=9,
IF (Y lt 1 and X gt 3) RZONE=9, and
IF (Y lt 0-1 and X gt 1) RZONE=10,
wherein ge is greater than or equal,
wherein le is less than or equal,
wherein lt is less than,
wherein gt is greater than,
wherein the output of this computation is a zone, coded as follows:
1-uE 2-uD 3-uC 4-uB 5-uA 6-lA 7-lB 8-lC 9-lD 10-lE.

20. The method of claim 13, wherein said glucose monitoring sensor comprises at least one of Beckman glucose analyzes, glucose oxidase analyzer, YSI Instruments analyzer and finger stick glucose meters, or any combination thereof.

21. The method of claim 7, wherein said point error-grid analysis (P-EGA) includes:
scatter plotting said point error-grid analysis (P-EGA) for said sensor BG rate against a reference BG rate computed from the data of a reference monitoring device, wherein said scatter plot is divided into $A_P$, $B_P$, $C_P$, $D_P$, and $E_P$ zones, wherein suffix "P" stands for point.

22. The method of claim 21, wherein
said $B_P$ zone is divided into upper $B_P$ zone and lower $B_P$ zone;
said $C_P$ zone is divided into upper $C_P$ zone and lower $C_P$ zone;
said $D_P$ zone is divided into upper $D_P$ zone and lower $D_P$ zone; and
said $E_P$ zone is divided into upper $E_P$ zone and lower $E_P$ zone.

23. The method of claim 22, wherein said point error-grid analysis (P-EGA) includes:

said zones are defined depending on the reference rate of BG change classified as follows:
(a) slow change range;
(b) moderate decrease range;
(c) moderate increase range;
(d) rapid decrease range; and
(e) rapid increase range.

24. The method of claim 23, wherein said classification of reference BG change comprises:
(a) said slow change range being about −1 and about 1 mg/dl/min;
(b) moderate decrease range being about −2 and about −1 mg/dl/min;
(c) moderate increase range being about 1 and about 2 mg/dl/min;
(d) rapid decrease range being less than about −2 mg/dl/min; and
(e) rapid increase range being greater than about 2 mg/dl/min.

25. The method of claim 24, wherein said point error-grid analysis (P-EGA) includes:
said zones are defined depending on the reference rate of BG change as follows:
(a) if the reference BG rate is within said slow change range, said P-EGA zones are identical to the zones of the conventional EGA;
(b) if the reference BG is falling at a rate within said moderate increase range, the upper limits of upper said $A_P$, $B_P$, and $D_P$ zones are expanded by about 10 mg/dl, and if the reference BG is falling faster than said rapid decrease range, the upper limits of upper $A_P$, $B_P$, and $D_P$ zones are expanded by about 20 mg/dl; and
(c) if the reference BG is rising at a rate within said moderate increase, the lower limits of lower $A_P$, $B_P$, and $D_P$ zones are expanded by about 10 mg/dl, and if the reference BG is rising faster than said rapid increase range, the lower limits of lower said $A_P$, $B_P$, and $D_P$ zones are expanded by about 20 mg/dl.

26. The method of claim 23, wherein said point error-grid analysis (P-EGA) further includes:
computing said P-EGA zones for each pair of said reference-sensor BG readings using the formulas below:
a) if the BG rate of change is in said slow change range, apply the formulas:
wherein U1 is abbreviated for said Reference BG,
wherein W1 is abbreviated for said Sensor BG,
IF (W1 ge U1) ZONE0=5,
IF (W1 ge 1.20 U1 and U1 gt 70) ZONE0=4,
IF (W1 ge (1.03 U1+107.9) and U1 gt 70) ZONE0=3,
IF (W1 ge 1.20 U1 and W1 gt 70 and U1 le 70) ZONE0=2,
IF (W1 ge 180 and U1 le 70) ZONE0=1,
IF (W1 lt U1) ZONE0=6,
IF (W1 le 0.8 U1 and U1 gt 70) ZONE0=7,
IF (W1 le (1.4 U1-182) and U1 le 180) ZONE0=8,
IF (U1 ge 240 and W1 gt 70 and W1 lt 180) ZONE0=9, and
IF (U1 gt 180 and W1 le 70) ZONE0=10;
b) if BG is falling at said moderate rate apply the formulas:
wherein U2 is abbreviated for said Reference BG,
wherein W2 is abbreviated for said Sensor BG,
IF (W2 ge U2) ZONE2=5,
IF (W2 ge (1.20 U2+10) and U2 gt 70) ZONE2=4,
IF (W2 ge (1.03 U2+117.9) and U2 gt 70) ZONE2=3,
IF (W2 ge (1.20 U2+10) and W2 gt 80 and U2 le 70) ZONE2=2,
IF (W2 ge 190 and U2 le 70) ZONE2=1,
IF (W2 lt U2) ZONE2=6,
IF (W2 le 0.8 U2 and U2 gt 70) ZONE2=7,
IF (W2 le (1.4 U2-182) and U2 le 180) ZONE2=8,
IF (U2 ge 240 and W2 gt 70 and W2 lt 180) ZONE2=9, and
IF (U2 gt 180 and W2 le 70) ZONE2=10;
c) if BG is falling at said rapid rate use the formulas:
wherein U4 is abbreviated for said Reference BG,
wherein W4 is abbreviated for said Sensor BG,
IF (W4 ge U4) ZONE4=5,
IF (W4 ge (1.20 U4+20) and U4 gt 70) ZONE4=4,
IF (W4 ge (1.03 U4+127.9) and U4 gt 70) ZONE4=3,
IF (W4 ge (1.20 U4+20) and W4 gt 90 and U4 le 70) ZONE4=2,
IF (W4 ge 200 and U4 le 70) ZONE4=1,
IF (W4 lt U4) ZONE4=6,
IF (W4 le 0.8 U4 and U4 gt 70) ZONE4=7,
IF (W4 le (1.4 U4-182) and U4 le 180) ZONE4=8,
IF (U4 ge 240 and W4 gt 70 and W4 lt 180) ZONE4=9, and
IF (U4 gt 180 and W4 le 70) ZONE4=10;
d) if BG is rising at said moderate rate use the formulas:
wherein U1 is abbreviated for said Reference BG,
wherein SENBG is abbreviated for said Sensor BG,
IF (W1 ge U1) ZONE1=5,
IF (W1 ge 1.20 U1 and U1 gt 70) ZONE1=4,
IF (W1 ge (1.03 U1+107.9) and U1 gt 70) ZONE1=3,
IF (W1 ge 1.20 U1 and W1 gt 70 and U1 le 70) ZONE1=2,
IF (W1 ge 180 and U1 le 70) ZONE1=1,
IF (W1 lt U1) ZONE1=6,
IF (W1 le (0.8 U1-10) and U1 gt 70) ZONE1=7,
IF (W1 le (1.4 U1-192) and U1 le 180) ZONE1=8,
IF (U1 ge 240 and W1 gt 60 and W1 lt 170) ZONE1=9, and
IF (U1 gt 180 and W1 le 60) ZONE1=10; and
e) if BG is rising at said rapid rate use the formulas:
wherein U3 is abbreviated for said Reference BG,
wherein W3 is abbreviated for said Sensor BG,
IF (W3 ge U3) ZONE3=5,
IF (W3 ge 1.20 U3 and U3 gt 70) ZONE3=4,
IF (W3 ge (1.03 U3+107.9) and U3 gt 70) ZONE3=3,
IF (W3 ge 1.20 U3 and W3 gt 70 and U3 le 70) ZONE3=2,
IF (W3 ge 180 and U3 le 70) ZONE3=1,
IF (W3 lt U3) ZONE3=6. U3 gt 70) ZONE3=7,
IF (W3 le (1.4 U3-202) and U3 le 180) ZONE3=8,
IF (U3 ge 240 and W3 gt 50 and W3 lt 160) ZONE3=9,
IF (U3 gt 180 and W3 le 50) ZONE3=10, and
IF (W3 le (0.8 U3-20),
wherein ge is greater than or equal,
wherein le is less than or equal,
wherein lt is less than,
wherein gt is greater than,
wherein the output of this computation is a zone, coded as follows:
1-uE, 2-uD, 3-uC, 4-uB, 5-uA, 6-lA, 7-lB, 8-lC, 9-lD, 10-lE.

27. The method of claim 7, further comprising:
splitting reference BG values received from a reference BG monitoring device into three clinically meaningful regions including hypoglycemia, euglycemia and hyperglycemia regions; and
combining results from the rate error-grid analysis (R-EGA) and point error-grid analysis (P-EGA) within each of these regions.

28. The method of claim 27, wherein:
said hypoglycemia region is defined as BG<=70 mg/dl (3.9 mmol/l);
said euglycemia region is defined as 70 mg/dl (3.9 mmol/l)<BG<180 mg/dl (10 mmol/l), and
said hyperglycemia region defined as BG>180 mg/dl (10 mmol/l).

29. The method of claim 28, further comprising:
providing a table showing a relationship between said R-EGA and P-EGA values of said sensor in a hypoglycemic range including rows of said R-EGA values and columns of P-EGA values wherein said table indicates percentages of accurate sensor readings, benign error sensor readings, and erroneous sensor readings.

30. The method of claim 29, wherein said R-EGA and P-EGA values will be considered accurate if a value falls in an $A_P$ zone of an P-EGA column of the table and said same value falls in an $A_R$ or $B_R$ zone of R-EGA rows of the table.

31. The method of claim 29, wherein said R-EGA and P-EGA values will be considered clinically erroneous if a value falls in a
$D_P$ zone or $E_P$ zone of a P-EGA column of the table, or
$A_P$ zone of a P-EGA column of the table and said same value falls in a uD or uE zones of R-EGA rows of the table.

32. The method of claim 29, wherein said R-EGA and P-EGA values will be considered benign errors if a value falls in an $A_P$ zone of a P-EGA column of the table and said same value falls in uC, lC, lD, or lE zones of R-EGA rows of the table.

33. The method of claim 29, further comprising:
providing a table showing a relationship between said R-EGA and P-EGA values of said sensor in a euglycemia range including rows of said R-EGA values and columns of P-EGA values wherein said table indicates percentages of accurate sensor readings, benign error sensor readings, and erroneous sensor readings.

34. The method of claim 33, wherein said R-EGA and P-EGA values will be considered accurate if a value falls in an $A_P$ zone or $B_P$ zone of P-EGA columns of the table and said same value falls in $A_R$ or $B_R$ zones of R-EGA rows of the table.

35. The method of claim 33, wherein said R-EGA and P-EGA values will be considered clinically erroneous if a value falls in the $A_P$ zone or $B_P$ zone of the P-EGA columns of the table and said same value falls in uE or lE of R-EGA rows of the table; or $C_P$ zone of a P-EGA column of the table.

36. The method of claim 33, wherein said R-EGA and P-EGA values will be considered benign errors if a value falls in the $A_P$ zone or $B_P$ zone of the P-EGA columns of the table and said same value falls in the uC, lC, uD or lD of the R-EGA rows of the table.

37. The method of claim 33, further comprising:
providing a table showing a relationship between said R-EGA and P-EGA values of said sensor in a hyperglycemia range including rows of said R-EGA values and columns of P-EGA values wherein said table indicates percentages of accurate sensor readings, benign error sensor readings, and erroneous sensor readings.

38. The method of claim 37, wherein said R-EGA and P-EGA values will be considered accurate if a value falls in an $A_P$ zone or $B_P$ zone of the P-EGA columns of the table and said same value falls in $A_R$ or $B_R$ zones of the R-EGA rows of the table.

39. The method of claim 37, wherein said R-EGA and P-EGA values will be considered clinically erroneous if a value falls in an $A_P$ zone or $B_P$ zone of the P-EGA columns of the table and said same value falls in lD, uE or lE of the R-EGA rows of the table; or $C_P$ zone, $D_P$ zone or $E_P$ zone of the P-EGA column of the table.

40. The method of claim 37, wherein said R-EGA and P-EGA values will be considered benign errors if a value falls in an $A_P$ zone or $B_P$ zone of the P-EGA columns of the table and said same value falls in uC, lC or uD of the R-EGA rows of the table.

41. The method of claim 37, comprising:
combining the results from tables of claims 28, 32 and 36 into a single accuracy estimate of a sensor using a linear weighted combination.

42. The method of claim 41, said combining of the R-EGA and P-EGA zone as according to the following formulas:

$$A(\text{Accurate Readings}) = w1*A1 + w2*A2 + w3*A3,$$

$$B(\text{Benign Errors}) = w1*B1 + w2*B2 + w3*B3,$$

$$Err(\text{Erroneous Readings}) = w1*Err1 + w2*Err2 + w3*Err3, \text{ wherein:}$$

A1, B1, Err1 are percentages of accurate readings, benign errors, and erroneous readings during hypoglycemia;
A2, B2, Err2 are the percentages of accurate readings, benign errors, and erroneous readings during euglycemia, and
A3, B3, Err3 are the percentages of accurate readings, benign errors, and erroneous readings during hyperglycemia, and wherein the weights w1, w2, w3 are assigned to the hypoglycemic, euglycemic, and hyperglycemic BG ranges.

43. The method of claim 42, wherein said weights are about 0.07, about 0.53, and about 0.40 for hypoglycemic, euglycemic, and hyperglycemic ranges, respectively.

44. A system for evaluating accuracy of a glucose monitoring sensor, said system comprising a microprocessor programmed to perform the following:
evaluate point accuracy of blood glucose (BG) values received from said monitoring sensor;
evaluate accuracy of direction and rate of BG fluctuations received from said monitoring sensor; and
combine said point accuracy and rate accuracy in an estimate of sensor precision.

45. The system of claim 44, wherein said estimate of sensor precision comprises:
performing a combination of three grids adapted specifically for hypoglycemic, euglycemic, and hyperglycemic BG ranges.

46. The system of claim 45, wherein said estimate of sensor precision includes solely a single estimate using a weighted combination of hypoglycemic, euglycemic, hyperglycemic BG ranges.

47. The system of claim 45, wherein said estimate of sensor precision includes a plurality of estimates using a weighted combination of hypoglycemic, euglycemic, hyperglycemic BG ranges.

48. The system of claim 44, wherein said system is for use with a subject, wherein said subject is a human or an animal.

49. The system of claim 44, wherein said sensor comprises a continuous glucose monitor or semi-continuous glucose monitor or combination of both.

50. The system of claim 44, wherein:
said accuracy evaluation of direction and rate of BG fluctuations includes performing rate error-grid analysis (R-EGA), and
said accuracy evaluation blood glucose (BG) values includes performing point error-grid analysis (P-EGA) that determines correct presentation of said blood glucose (BG) values.

51. The system of claim 50, wherein said estimate of sensor precision comprises:

performing a combination of three grids adapted specifically for hypoglycemic, euglycemic, and hyperglycemic BG ranges.

52. The system of claim 51, wherein said estimate of sensor precision includes solely a single estimate using a weighted combination of hypoglycemic, euglycemic, hyperglycemic BG ranges.

53. The system of claim 51, wherein said estimate of sensor precision includes a plurality of estimates using a weighted combination of hypoglycemic, euglycemic, hyperglycemic BG ranges.

54. The system of claim 50, wherein system is for use with a subject, wherein said subject is a human or an animal.

55. The system of claim 50, wherein said sensor comprises a continuous glucose monitor or semi-continuous glucose monitor or combination of both.

56. The system of claim 50, wherein said rate error-grid analysis (R-EGA) includes:
for each pair of reference BG points, $RBG(t_1)$ and $RBG(t_2)$ received from a reference blood glucose monitoring device, taken at times $t_1$ and $t_2$, a reference BG rate is estimated as the ratio of the change in the BG points divided by the length of the elapsed time interval as follows:

reference $BG$ rate of change (mg/dl/min)=$(RBG(t_2)-RBG(t_1))/(t_2-t_1)$.

57. The system of claim 56, wherein said rate said error-grid analysis (R-EGA) further includes:
for each pair of sensor reported BG points, $SBG(t_1)$ and $SBG(t_2)$, received from said glucose monitoring sensor, taken at times $t_1$ and $t_2$, a sensor BG rate is estimated as:

sensor $BG$ rate of change (mg/dl/min)=$(SBG(t_2)-SBG(t_1))/(t_2-t_1)$.

58. The system of claim 57, wherein said rate said error-grid analysis (R-EGA) further includes:
scatter plotting said sensor BG rate of change against said reference BG rate of change.

59. The system of claim 58, wherein said rate said error-grid analysis (R-EGA) further includes dividing said scatter plot into accuracy zones.

60. The system of claim 59, wherein said accuracy zones comprise A through E accuracy zones, which have a clinical meaning similar to the clinical meaning of the conventional Error Grid Analysis (EGA).

61. The system of claim 60, wherein said clinical meanings are defined as follows:
(a) AR-zone (accurate);
(b) CR-zone (over-correction);
(c) DR-zone (failure to detect);
(d) ER-zone (erroneous reading); and
(e) BR-zone (benign errors),
wherein suffix R stands for rate.

62. The system of claim 61, wherein said rate error-grid analysis (R-EGA) further includes:
computing said R-EGA zones for each pair of said reference-sensor BG rates of change using the formulas below, wherein X is abbreviated for said reference BG rate of change and wherein Y is abbreviated for said sensor BG rate of change:
IF (Y ge X) RZONE=5,
IF (Y gt (X+1) and X ge 0-2 and X le 1) RZONE=4,
IF (Y gt 0.5× and X lt 0-2) RZONE=4,
IF (Y gt 2.0× and X gt 1) RZONE=4,
IF (Y gt (X+2) and X ge 0-1 and X lt 1) RZONE=3,
IF (Y gt (X+2) and X ge 0-3 and X lt 0-1) RZONE=2,
IF (Y gt 0-1 and X lt 0-3) RZONE=2,
IF (Y gt 1 and X lt 0-1) RZONE=1,
IF (Y lt X) RZONE=6,
IF (Y lt (X−1) and X ge 0-1 and X le 2) RZONE=7,
IF (Y lt 2.0 X and X lt 0-1) RZONE=7,
IF (Y lt 0.5 X and X gt 2) RZONE=7,
IF (Y lt (X−2) and X ge 0-1 and X le 1) RZONE=8,
IF (Y lt (X−2) and X gt 1 and X le 3) RZONE=9,
IF (Y lt 1 and X gt 3) RZONE=9, and
IF (Y lt 0-1 and X gt 1) RZONE=10,
wherein ge is greater than or equal,
wherein le is less than or equal,
wherein lt is less than,
wherein gt is greater than,
wherein the output of this computation is a zone, coded as follows:
1-uE 2-uD 3-uC 4-uB 5-uA 6-lA 7-lB 8-lC 9-lD 10-lE.

63. The system of claim 56, wherein said glucose monitoring sensor comprises at least one of Beckman glucose analyzes, glucose oxidase analyzer, YSI Instruments analyzer and finger stick glucose meters, or any combination thereof.

64. The system of claim 50, wherein said point error-grid analysis (P-EGA) includes:
scatter plotting said point error-grid analysis (P-EGA) for said sensor BG rate against a reference BG rate computed from the data of a reference monitoring device, wherein said scatter plot is divided into $A_P$, $B_P$, $C_P$, $D_P$, and $E_P$ zones, wherein suffix "P" stands for point.

65. The system of claim 64, wherein
said $B_P$ zone is divided into upper $B_P$ zone and lower $B_P$ zone;
said $C_P$ zone is divided into upper $C_P$ zone and lower $C_P$ zone;
said $D_P$ zone is divided into upper $D_P$ zone and lower $D_P$ zone; and
said $E_P$ zone is divided into upper $E_P$ zone and lower $E_P$ zone.

66. The system of claim 65, wherein said point error-grid analysis (P-EGA) includes:
said zones are defined depending on the reference rate of BG change classified as follows:
(a) slow change range;
(b) moderate decrease range;
(c) moderate increase range;
(d) rapid decrease range; and
(e) rapid increase range.

67. The system of claim 66, wherein said classification of reference BG change comprises:
(a) said slow change range being about −1 and about 1 mg/dl/min;
(b) moderate decrease range being about −2 and about −1 mg/dl/min;
(c) moderate increase range being about 1 and about 2 mg/dl/min;
(d) rapid decrease range being less than about −2 mg/dl/min; and
(e) rapid increase range being greater than about 2 mg/dl/min.

68. The system of claim 67, wherein said point error-grid analysis (P-EGA) includes:
said zones are defined depending on the reference rate of BG change as follows:
(a) if the reference BG rate is within said slow change range, said P-EGA zones are identical to the zones of the conventional EGA;
(b) if the reference BG is falling at a rate within said moderate increase range, the upper limits of upper said $A_P$, $B_P$, and $D_P$ zones are expanded by about 10 mg/dl, and if the reference BG is falling faster than said rapid decrease range, the upper limits of upper $A_P$, $B_P$, and $D_P$ zones are expanded by about 20 mg/dl; and (c) if the reference BG is rising at a rate within said moderate increase, the lower limits of lower $A_P$, $B_P$, and $D_P$ zones are expanded by about 10 mg/dl, and if the reference BG is rising faster than said rapid increase range, the lower limits of lower said $A_P$, $B_P$, and $D_P$ zones are expanded by about 20 mg/dl.

69. The system of claim 66, wherein said point error-grid analysis (P-EGA) further includes:

computing said P-EGA zones for each pair of said reference-sensor BG readings using the formulas below:

a) if the BG rate of change is in said slow change rate, apply the formulas:
wherein U1 is abbreviated for said Reference BG,
wherein W1 is abbreviated for said Sensor BG,
IF (W1 ge U1) ZONE0=5,
IF (W1 ge 1.20 U1 and U1 gt 70) ZONE0=4,
IF (W1 ge (1.03 U1+107.9) and U1 gt 70) ZONE0=3,
IF (W1 ge 1.20 U1 and W1 gt 70 and U1 le 70) ZONE0=2,
IF (W1 ge 180 and U1 le 70) ZONE0=1,
IF (W1 lt U1) ZONE0=6,
IF (W1 le 0.8 U1 and U1 gt 70) ZONE0=7,
IF (W1 le (1.4 U1-182) and U1 le 180) ZONE0=8,
IF (U1 ge 240 and W1 gt 70 and W1 lt 180) ZONE0=9, and
IF (U1 gt 180 and W1 le 70) ZONE0=10;

b) if BG is falling said moderate rate apply the formulas:
wherein U2 is abbreviated for said Reference BG,
wherein W2 is abbreviated for said Sensor BG,
IF (W2 ge U2) ZONE2=5,
IF (W2 ge (1.20 U2+10) and U2 gt 70) ZONE2=4,
IF (W2 ge (1.03 U2+117.9) and U2 gt 70) ZONE2=3,
IF (W2 ge (1.20 U2+10) and W2 gt 80 and U2 le 70) ZONE2=2,
IF (W2 ge 190 and U2 le 70) ZONE2=1,
IF (W2 lt U2) ZONE2=6,
IF (W2 le 0.8 U2 and U2 gt 70) ZONE2=7,
IF (W2 le (1.4 U2-182) and U2 le 180) ZONE2=8,
IF (U2 ge 240 and W2 gt 70 and W2 lt 180) ZONE2=9, and
IF (U2 gt 180 and W2 le 70) ZONE2=10;

c) if BG is falling at said rapid rate use the formulas:
wherein U4 is abbreviated for said Reference BG,
wherein W4 is abbreviated for said Sensor BG,
IF (W4 ge U4) ZONE4=5,
IF (W4 ge (1.20 U4+20) and U4 gt 70) ZONE4=4,
IF (W4 ge (1.03 U4+127.9) and U4 gt 70) ZONE4=3,
IF (W4 ge (1.20 U4+20) and W4 gt 90 and U4 le 70) ZONE4=2,
IF (W4 ge 200 and U4 le 70) ZONE4=1,
IF (W4 lt U4) ZONE4=6,
IF (W4 le 0.8 U4 and U4 gt 70) ZONE4=7,
IF (W4 le (1.4 U4-182) and U4 le 180) ZONE4=8,
IF (U4 ge 240 and W4 gt 70 and W4 lt 180) ZONE4=9, and
IF (U4 gt 180 and W4 le 70) ZONE4=10;

d) if BG is rising at said moderate rate of use the formulas:
wherein U1 is abbreviated for said Reference BG,
wherein SENBG is abbreviated for said Sensor BG,
IF (W1 ge U1) ZONE1=5,
IF (W1 ge 1.20 U1 and U1 gt 70) ZONE1=4,
IF (W1 ge (1.03 U1+107.9) and U1 gt 70) ZONE1=3,
IF (W1 ge 1.20 U1 and W1 gt 70 and U1 le 70) ZONE1=2,
IF (W1 ge 180 and U1 le 70) ZONE1=1,
IF (W1 lt U1) ZONE1=6,
IF (W1 le (0.8 U1-10) and U1 gt 70) ZONE1=7,
IF (W1 le (1.4 U1-192) and U1 le 180) ZONE1=8,
IF (U1 ge 240 and W1 gt 60 and W1 lt 170) ZONE1=9, and
IF (U1 gt 180 and W1 e 60) ZONE1=10; and e) if BG is rising at said rapid rate use the formulas:
wherein U3 is abbreviated for said Reference BG,
wherein W3 is abbreviated for said Sensor BG,
IF (W3 ge U3) ZONE3=5,
IF (W3 ge 1.20 U3 and U3 gt 70) ZONE3=4,
IF (W3 ge (1.03 U3+107.9) and U3 gt 70) ZONE3=3,
IF (W3 ge 1.20 U3 and W3 gt 70 and U3 le 70) ZONE3=2,
IF (W3 ge 180 and U3 le 70) ZONE3=1,
IF (W3 lt U3) ZONE3=6. U3 gt 70) ZONE3=7,
IF (W3 le (1.4 U3-202) and U3 le 180) ZONE3=8,
IF (U3 ge 240 and W3 gt 50 and W3 lt 160) ZONE3=9,
IF (U3 gt 180 and W3 le 50) ZONE3=10, and
IF (W3 le (0.8 U3-20), wherein ge is greater than or equal,
wherein le is less than or equal,
wherein lt is less than,
wherein gt is greater than,
wherein the output of this computation is a zone, coded as follows:
1-uE, 2-uD, 3-uC, 4-uB, 5-uA, 6-lA, 7-lB, 8-lC, 9-lD, 10-lE.

70. The system of claim 50, further comprising:
splitting reference BG values received from a reference BG monitoring device into three clinically meaningful regions including hypoglycemia, euglycemia and hyperglycemia regions; and
combining results from the rate error-grid analysis (R-EGA) and point error-grid analysis (P-EGA) within each of these regions.

71. The system of claim 70, wherein:
said hypoglycemia region is defined as BG<=70 mg/dl (3.9 mmol/l);
said euglycemia region is defined as 70 mg/dl (3.9 mmol/l)<BG<180 mg/dl (10 mmol/l), and
said hyperglycemia region defined as BG>180 mg/dl (10 mmol/l).

72. The system of claim 71, further comprising:
providing a table showing a relationship between said R-EGA and P-EGA values of said sensor in a hypoglycemic range including rows of said R-EGA values and columns of P-EGA values wherein said table indicates percentages of accurate sensor readings, benign error sensor readings, and erroneous sensor readings.

73. The system of claim 72, wherein said R-EGA and P-EGA values will be considered accurate if a value falls in an $A_P$ zone of the P-EGA column of the table and said same value falls in AR or BR zones of the R-EGA rows of the table.

74. The system of claim 72, wherein said R-EGA and P-EGA values will be considered clinically erroneous if a value falls in a $D_P$ zone or $E_P$ zone of the P-EGA column of the table, or $A_P$ zone of the P-EGA column of the table and said same value falls in uD or uE zones of the R-EGA rows of the table.

75. The system of claim 72, wherein said R-EGA and P-EGA values will be considered benign errors if a value falls in an $A_P$ zone of the P-EGA column of the table and said same value falls in uC, lC, lD, or lE zones of the R-EGA rows of the table.

76. The system of claim 72, further comprising:
providing a table showing a relationship between said R-EGA and P-EGA values of said sensor in a euglycemia range including rows of said R-EGA values and columns of P-EGA values wherein said table indicates percentages of accurate sensor readings, benign error sensor readings, and erroneous sensor readings.

77. The system of claim 76, wherein said R-EGA and P-EGA values will be considered accurate if a value falls in an $A_P$ zone or $B_P$ zone of the P-EGA columns of the table and said same value falls in $A_R$ or $B_R$ zones of the R-EGA rows of the table.

78. The system of claim 76, wherein said R-EGA and P-EGA values will be considered clinically erroneous if a value falls in an $A_P$ zone or $B_P$ zone of the P-EGA columns of the table and said same value falls in the uE or lE of the R-EGA rows of the table; or $C_P$ zone of the P-EGA column of the table.

79. The system of claim 76, wherein said R-EGA and P-EGA values will be considered benign errors if a value falls in an $A_P$ zone or $B_P$ zone of the P-EGA columns of the table and said same value falls in $_{the}$ uC, lC, uD or lD of the R-EGA rows of the table.

80. The system of claim 76, further comprising:
providing a table showing a relationship between said R-EGA and P-EGA values of said sensor in a hyperglycemia range including rows of said R-EGA values and columns of P-EGA values wherein said table indicates percentages of accurate sensor readings, benign error sensor readings, and erroneous sensor readings.

81. The system of claim 80, wherein said R-EGA and P-EGA values will be considered accurate if a value falls in an $A_P$ zone or $B_P$ zone of the P-EGA columns of the table and said same value falls in $A_R$ or $B_R$ zones of the R-EGA rows of the table.

82. The system of claim 80, wherein said R-EGA and P-EGA values will be considered clinically erroneous if a value falls in an $A_P$ zone or $B_P$ zone of the P-EGA columns of the table and said same value falls in the lD, uE or lE zones of the R-EGA rows of the table; or $C_P$ zone, $D_P$ zone or $E_P$ zone of the P-EGA column of the table.

83. The system of claim 80, wherein said R-EGA and P-EGA values will be considered benign errors if a value falls in an $A_P$ zone or $B_P$ zone of the P-EGA columns of the table and said same value falls in uC, lC or uD zones of the R-EGA rows of the table.

84. The system of claim 80, comprising:
combining the results from tables of claims 69, 73 and 77 into a single accuracy estimate of a sensor using a linear weighted combination.

85. The system of claim 84, said combining of the R-EGA and P-EGA zone as according to the following formulas:

$$A(\text{Accurate Readings}) = w1*A1 + w2*A2 + w3*A3,$$

$$B(\text{Benign Errors}) = w1*B1 + w2*B2 + w3*B3,$$

$$Err(\text{Erroneous Readings}) = w1*Err1 + w2*Err2 + w3*Err3, \text{ wherein:}$$

A1, B1, Err1 are percentages of accurate readings, benign errors, and erroneous readings during hypoglycemia;
A2, B2, Err2 are the percentages of accurate readings, benign errors, and erroneous readings during euglycemia, and
A3, B3, Err3 are the percentages of accurate readings, benign errors, and erroneous readings during hyperglycemia, and wherein the weights w1, w2, w3 are assigned to the hypoglycemic, euglycemic, and hyperglycemic BG ranges.

86. The method of claim 85, wherein said weights are about 0.07, about 0.53, and about 0.40 for hypoglycemic, euglycemic, and hyperglycemic ranges, respectively.

87. A computer program product comprising a computer usable medium having computer program logic for enabling at least one processor in a computer system to evaluate accuracy of a glucose monitoring sensor, said computer program logic comprising:
evaluating point accuracy of blood glucose (BG) values received from said monitoring sensor;
evaluating accuracy of direction and rate of BG fluctuations received from said monitoring sensor; and
combining said point accuracy and rate accuracy in an estimate of sensor precision.

88. The computer program product of claim 87, wherein said estimate of sensor precision comprises:
performing a combination of three grids adapted specifically for hypoglycemic, euglycemic, and hyperglycemic BG ranges.

89. The computer program product of claim 88, wherein said estimate of sensor precision includes solely a single estimate using a weighted combination of hypoglycemic, euglycemic, hyperglycemic BG ranges.

90. The computer program product of claim 88, wherein said estimate of sensor precision includes a plurality of estimates using a weighted combination of hypoglycemic, euglycemic, hyperglycemic BG ranges.

91. The computer program product of claim 87, wherein said computer program product is for use with a subject, wherein said subject is a human or an animal.

92. The computer program product of claim 87, wherein said sensor comprises a continuous glucose monitor or semi-continuous glucose monitor or combination of both.

93. The computer program product of claim 87, wherein:
said accuracy evaluation of direction and rate of BG fluctuations includes performing rate error-grid analysis (R-EGA), and
said accuracy evaluation blood glucose (BG) values includes performing point error-grid analysis (P-EGA) that determines correct presentation of said blood glucose (BG) values.

94. The computer program product of claim 93, wherein said estimate of sensor precision comprises:
performing a combination of three grids adapted specifically for hypoglycemic, euglycemic, and hyperglycemic BG ranges.

95. The computer program product of claim 94, wherein said estimate of sensor precision includes solely a single estimate using a weighted combination of hypoglycemic, euglycemic, hyperglycemic BG ranges.

96. The computer program product of claim 94, wherein said estimate of sensor precision includes a plurality of estimates using a weighted combination of hypoglycemic, euglycemic, hyperglycemic BG ranges.

97. The computer program product of claim 93, wherein said computer program product is for use with a subject, wherein said subject is a human or an animal.

98. The computer program product of claim 93, wherein said sensor comprises a continuous glucose monitor or semi-continuous glucose monitor or combination of both.

99. A system for evaluating accuracy of a glucose monitoring sensor, said system comprising:
said glucose monitoring sensor; and
a microprocessor programmed to perform the following:
evaluate point accuracy of blood glucose (BG) values received from said monitoring sensor;
evaluate accuracy of direction and rate of BG fluctuations received from said monitoring sensor; and
combine said point accuracy and rate accuracy in an estimate of sensor precision.

100. A system for evaluating accuracy of a glucose monitoring sensor, said system comprising:

said glucose monitoring sensor;
a reference device; and
a microprocessor programmed to perform the following:
  evaluate point accuracy of blood glucose (BG) values received from said monitoring sensor;
  evaluate accuracy of direction and rate of BG fluctuations received from said monitoring sensor; and
  combine said point accuracy and rate accuracy in an estimate of sensor precision.

* * * * *